United States Patent
Fiering et al.

(10) Patent No.: US 11,291,756 B2
(45) Date of Patent: Apr. 5, 2022

(54) ACOUSTIC SEPARATION FOR BIOPROCESSING

(71) Applicant: THE CHARLES STARK DRAPER LABORATORY, INC., Cambridge, MA (US)

(72) Inventors: Jason O. Fiering, Boston, MA (US); Kenneth T. Kotz, Newton, MA (US); Nathan Francis Moore, Canton, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 232 days.

(21) Appl. No.: 16/452,191

(22) Filed: Jun. 25, 2019

(65) Prior Publication Data
US 2019/0307946 A1    Oct. 10, 2019

Related U.S. Application Data

(63) Continuation-in-part of application No. 16/302,429, filed as application No. PCT/US2017/030232 on Apr. 28, 2017.
(Continued)

(51) Int. Cl.
*A61M 1/36* (2006.01)
*B01L 3/00* (2006.01)
(Continued)

(52) U.S. Cl.
CPC ........ *A61M 1/3678* (2014.02); *A61M 1/3693* (2013.01); *B01L 3/502753* (2013.01);
(Continued)

(58) Field of Classification Search
CPC .. A61M 1/678; A61M 1/3678; A61M 1/3693; A61M 1/362; A61M 1/3616;
(Continued)

(56) References Cited

U.S. PATENT DOCUMENTS

| | | | |
|---|---|---|---|
| 9,663,756 B1 | 5/2017 | Lipkens et al. | |
| 10,370,635 B2 * | 8/2019 | Lipkens | ........ C12M 47/02 |

(Continued)

FOREIGN PATENT DOCUMENTS

| | | |
|---|---|---|
| JP | 2007/504446 A | 3/2007 |
| JP | 2012513287 A | 6/2012 |

(Continued)

OTHER PUBLICATIONS

Cushing et al. "Elastomeric Negative Acoustic Contrast Particles for Affinity Capture Assays", Analytical Chemistry (2013) vol. 85, pp. 2208-2215.
(Continued)

*Primary Examiner* — Michael McCullough
*Assistant Examiner* — Jessica L Burkman
(74) *Attorney, Agent, or Firm* — Lando & Anastasi, LLP

(57) ABSTRACT

A method for separating cells in a biofluid includes pretreating the biofluid by introducing an additive comprising a cell activator, flowing the pretreated biofluid through a microfluidic separation channel, and applying acoustic energy to the microfluidic separation channel to accumulate target cells in a primary stream and non-target cells in a secondary stream. A system for microfluidic cell separation capable of separating target cells from non-target cells in a biofluid includes at least one microfluidic separation channel, a source of biofluid, a source of additive comprising a cell activator, and at least one acoustic transducer coupled to the microfluidic separation channel.

21 Claims, 8 Drawing Sheets

Related U.S. Application Data

(60) Provisional application No. 62/367,773, filed on Jul. 28, 2016, provisional application No. 62/689,662, filed on Jun. 25, 2018.

(51) Int. Cl.
   *B03B 1/04*      (2006.01)
   *G01N 15/10*     (2006.01)

(52) U.S. Cl.
   CPC .......... *B01L 3/502761* (2013.01); *B03B 1/04* (2013.01); *A61M 2205/0244* (2013.01); *B01L 2200/0652* (2013.01); *B01L 2400/0436* (2013.01); *G01N 2015/1081* (2013.01)

(58) Field of Classification Search
   CPC .............. A61M 2205/0244; B03B 1/04; B01L 2200/0652; B01L 2400/0436; B01L 3/502753; B01L 2300/0864; G01N 2015/1081; G01N 1/40; G01N 1/4077; G01N 2001/4083; G01N 2001/4094; C02F 1/34; C02F 1/36; C02F 1/52; C02F 1/5209
   See application file for complete search history.

(56) References Cited

U.S. PATENT DOCUMENTS

| | | | | |
|---|---|---|---|---|
| 10,640,760 | B2* | 5/2020 | Lipkens | C12N 1/02 |
| 10,745,741 | B2* | 8/2020 | Utharala | B01L 7/52 |
| 10,962,525 | B2* | 3/2021 | Rendu | B01L 7/52 |
| 2007/0269887 | A1* | 11/2007 | Coelho | A61M 1/0209 435/366 |
| 2009/0029870 | A1* | 1/2009 | Ward | G01N 29/222 506/9 |
| 2011/0201099 | A1* | 8/2011 | Anderson | G01F 23/292 435/287.2 |
| 2012/0214224 | A1* | 8/2012 | Chan | B01F 13/0059 435/287.2 |
| 2013/0224777 | A1* | 8/2013 | Patzke | G01N 33/686 435/13 |
| 2013/0337529 | A1 | 12/2013 | Choo | |
| 2014/0069865 | A1* | 3/2014 | Yvert | C12N 1/00 210/611 |
| 2014/0230912 | A1 | 8/2014 | Aider et al. | |
| 2014/0273192 | A1 | 9/2014 | Sharpe et al. | |
| 2015/0017678 | A1 | 1/2015 | Matula et al. | |
| 2016/0030660 | A1 | 2/2016 | Sun et al. | |
| 2016/0103066 | A1* | 4/2016 | Schasfoort | G01N 35/08 506/9 |
| 2017/0042770 | A1 | 2/2017 | Warner et al. | |
| 2018/0362918 | A1* | 12/2018 | Lipkens | C12M 35/04 |
| 2020/0316603 | A1* | 10/2020 | Kashanin | B01L 3/502776 |

FOREIGN PATENT DOCUMENTS

| | | |
|---|---|---|
| WO | 2007128795 A2 | 11/2007 |
| WO | 2014046605 A1 | 3/2014 |
| WO | 2014/138739 A1 | 9/2014 |
| WO | 2016062975 A1 | 4/2016 |
| WO | WO-2018065626 A1 * | 4/2018 .......... G01N 33/491 |

OTHER PUBLICATIONS

Dykes et al. "Efficient Removal of Platelets from Peripheral Blood Progenitor Cell Products Using a Novel Micro-Chip Based Acoustophoretic Platform", PLOS One, (2011) vol. 6, No. 3, pp. E23074-1-10.

Grenvall et al., "Concurrent Isolation of Lymphocytes and Granulocytes Using Prefocused Free Flow Acoustophoresis", Anal. Chem., vol. 87, No. 11, 2015, pp. 5596-5604.

International Search Report and Written Opinion in application No. PCT/US2017/030232 dated Sep. 15, 2017.

International Search Report and Written Opinion in application No. PCT/US2018/029934 dated Oct. 8, 2018.

Invitation to Pay Additional Fees in application No. PCT/US2018/029934 dated Aug. 7, 2018.

Lenshof et al., "Efficient purification of CD4+ lymphocytes from peripheral blood progenitor cell products using affinity bead acoustophoresis", Cytometry Part A, vol. 85, No. 11, 2014, pp. 933-941.

Petersson et al., "Free Flow Acoustophoresis: Microfluidic-Based Mode of Particle and Cell Separation", Anal. Chem, vol. 79, No. 14, 2007, pp. 5117-5123.

Ye et al. "Separation of *Escherichia coli* Bacteria from Peripheral Blood Mononuclear Cells Using Standing Surface Acoutsitc Waves", Analytical Chemistry (2013) vol. 85, No. 19, pp. 9126-9134.

* cited by examiner

ACOUSTIC SEPARATION FOR BIOPROCESSING

CROSS-REFERENCE TO RELATED APPLICATIONS

This application is a continuation-in-part of U.S. patent application Ser. No. 16/302,429 titled "ACOUSTIC SEPARATION FOR BIOPROCESSING," filed on Nov. 16, 2018, which is a U.S. National Phase Application and claims the benefit under 35 U.S.C. § 371 of International Application No. PCT/US2017/030232, filed on Apr. 28, 2017, which claims priority to U.S. Provisional Application No. 62/367,773, filed on Jul. 28, 2016. This application claims priority under 35 U.S.C. § 119(e) to U.S. Provisional Patent Application No. 62/689,662, titled "ACOUSTIC SEPARATION FOR BIOPROCESSING," filed on Jun. 25, 2018. Each of these applications is hereby incorporated by reference in its entirety for all purposes.

FIELD OF TECHNOLOGY

Aspects and embodiments disclosed herein relate to systems and methods for the separation of cells. In particular, aspects and embodiments disclosed herein relate to systems and methods for the separation of target cells in a biofluid from non-target cells in the biofluid.

SUMMARY

In accordance with an aspect, there is provided a method of separating target cells from non-target cells in a biofluid. The method may comprise pretreating the biofluid by introducing an additive comprising a cell activator, flowing the pretreated biofluid into an inlet of a microfluidic separation channel, and applying acoustic energy to the microfluidic separation channel to accumulate target cells within a primary stream along the separation channel and accumulate non-target cells within a secondary stream along the separation channel. In some embodiments, pretreating the biofluid comprises introducing an additive into the biofluid to alter at least one of size of the target cells, size of the non-target cells, compressibility of the biofluid, compressibility of the target cells, compressibility of the non-target cells, aggregation potential of the target cells, and aggregation potential of the non-target cells. In some embodiments, the acoustic energy may be applied transverse to a direction of the fluid flow through the separation channel.

According to some embodiments, the method further comprises selecting the target cells to be leukocytes selected from the group consisting of mononuclear cells, lymphocytes, monocytes, granulocytes, agranulocytes, macrophages, T cells, B cells, NK cells, subclasses thereof, and combinations thereof. Thus, in accordance with one embodiment, there is provided a method of separating leukocytes from non-target cells. For instance, there is provided a method of separating B cells from non-target cells. For instance, there is a method of separating T cells from non-target cells.

The method may comprise selecting the cell activator to comprise a B cell activator. The method may comprise selecting the B cell activator to comprise CpG oligodeoxynucleotides.

The method may comprise selecting the cell activator to comprise a T cell activator. The method may comprise selecting the T cell activator to comprise at least one of a humanized CD3 and CD28 agonist bead and Interleukin 2.

In some embodiments, the additive may be selected from the group consisting of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

The cell aggregator may be a platelet activator or a cell adhesion molecule. In some embodiments, the platelet activator may be adenosine diphosphate.

In accordance with another aspect, there is provided a system for microfluidic cell separation. The system may be configured to separate target cells from non-target cells in a biofluid. In some embodiments, the system comprises at least one microfluidic separation channel comprising at least one inlet, a first outlet, and a second outlet, a source of biofluid in fluid communication with the microfluidic separation channel, a source of additive comprising a cell activator in fluid communication with the source of the biofluid, the source of the additive configured to introduce at least one additive into the biofluid, and at least one acoustic transducer coupled to a wall of the microfluidic separation channel. The additive may be capable of altering at least one of size of the target cells, size of the non-target cells, compressibility of the biofluid, compressibility of the target cells, compressibility of the non-target cells, aggregation potential of the target cells, and aggregation potential of the non-target cells.

The cell activator may comprise a B cell activator. The B cell activator may comprise CpG oligodeoxynucleotides.

The cell activator may comprise a T cell activator. The T cell activator may comprise at least one of a humanized CD3 and CD28 agonist bead and Interleukin 2.

In some embodiments, the source of the additive may be configured to introduce at least one additive selected from the group consisting of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

The second additive may comprise a cell aggregator selected from a platelet activator and a cell adhesion molecule. The platelet activator may comprise adenosine diphosphate.

The system may further comprise at least one input sensor configured to measure a concentration of target cells or non-target cells in the biofluid.

The system may further comprise at least one output sensor configured to measure at least one parameter of an output suspension. The at least one parameter of the output suspension may comprise at least one of hematocrit (HCT %) of the output suspension, concentration of target cells in the output suspension, and concentration of non-target cells in the output suspension.

In some embodiments, the system may further comprise a control module in electrical communication with the at least one input sensor, the at least one output sensor, and the source of the additive, configured to introduce a predetermined volume of the additive into the biofluid in response to a measurement of at least one of the concentration of the target cells or the non-target cells in the biofluid and the parameter of the output suspension being outside tolerance of a target value.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 is a micrograph of a microfluidic separation channel coupled to an acoustic transducer that is turned on;

DETAILED DESCRIPTION

Figure 1:
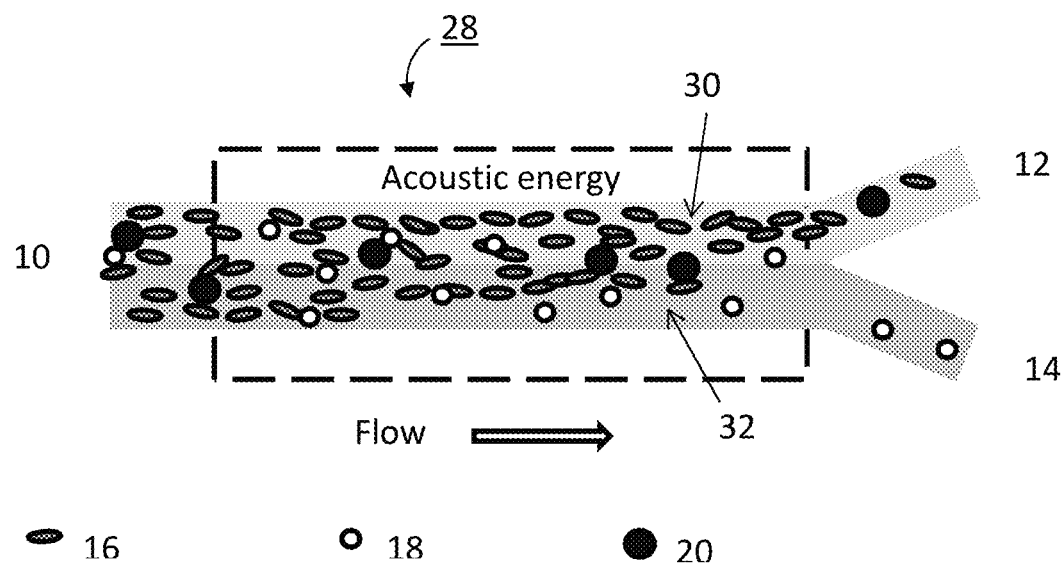
FIG. 1 is a schematic drawing of a microfluidic separation channel, according to one embodiment.

In the fields of cell therapy and bioprocessing emerging medical techniques may involve extraction of blood or tissue from a patient followed by purification of a particular cell type from a sample. In some applications, the particular cell type is prepared for treatment or manipulated before it is re-injected into a patient. Aspects and embodiments disclosed herein relate to separation of a desired cell type from a liquid suspension of mixed cell types. In particular, one example application is the separation of leukocytes or a subclass of leukocytes from a blood sample.

Aspects and embodiments disclosed herein may relate to methods and systems for use in processing of cells for cell therapy. Many other uses of some of the embodiments described herein could also be envisioned, in particular wherever a particular cell type is desired to be collected from a cell suspension or natural sample. Some non-limiting examples include the diagnostic or environmental monitoring assays, tissue engineering, in vitro models, and biomanufacturing systems, such as for energy applications.

Formerly cell selection for applications within bioprocessing has been performed by one or more batch centrifugations, continuous centrifugations, magnetic separation, or combinations thereof. Centrifugation is only able to separate particles by density, limiting its ability to separate leukocyte subclasses from other types of leukocytes. Addition of a density medium may improve leukocyte stratification, but only in small batch procedures requiring technically trained operators. Furthermore, no form of centrifugation is able to separate subclasses of lymphocytes such as T cells from B cells.

Magnetic separation can be highly selective, but depends on the attachment of paramagnetic capture particles to cells using affinity ligands, such as antibodies. The particles may pose a safety risk if injected into a patient. Accordingly, the magnetic particles must be removed from a final therapeutic product. The efficiency of magnetic separation varies with the load of interfering cells or with the concentration of background proteins contained in the sample that may specifically or non-specifically bind to the affinity ligand. Additionally, the attachment of certain magnetic particles to cells through affinity ligands may be irreversible. In this case, only one separation can be done using a general magnetic force. For these reasons, magnetic separation is a complex procedure that is usually insufficient for bioprocessing workflow.

Aspects and embodiments disclosed herein may be advantageous over previous cell separation technologies because, for example, in some embodiments the purification of desired cells can be performed continuously, in some embodiments, the systems and methods provide separation by both size and density to further enhance cell separation, in some embodiments the separation processes may be readily scaled to small or large sample volumes, in some embodiments, a high degree of purification can be achieved without the use of antibodies, ligands, immunochemistry, or other foreign particles, and in some embodiments, further purification can be achieved with the addition of safely injectable, physiologically acceptable additives.

One non-limiting example of cell therapy that may be performed using systems and methods described herein is CAR-T therapy for the treatment of blood cancers. The therapy may involve engineering chimeric antigen receptors on T-cells by viral transduction or other gene editing methods known to those skilled in the art. In CAR-T treatment, blood is generally collected from a patient. The blood may be whole blood, or leukapheresis product. Leukapheresis product is a collection of mainly leukocytes and platelets, with a reduced concentration of erythrocytes, as compared to whole blood. From this collected blood sample, specific subclasses of the leukocytes may be selected for further processing. In CAR-T therapy, the desired classes of cells may vary, but generally include mononuclear cells, lymphocytes, T cells, or subclasses of T cells, such as CD4+, or CD8+. The selected cells may then be modified (transduced)

by genetic engineering to enhance their ability to attack malignant cells. The genetic engineering may include incubating to increase their abundance, washing or purifying, testing for quality control, and optionally infusing into a patient.

The aspects and embodiments disclosed herein may improve methods for selecting the desired cells, and may also have applications in other steps in the process such as washing or the cells, or purification of samples after transduction.

Acoustic separation, also referred to as acoustophoresis, may be used to isolate or enrich desired cells as part of a bioprocessing workflow. Acoustic separation of particles in a biofluid has been described in, for example, U.S. Patent Application Publication Nos. 2016-0030660, 2016-0008532, and 2013-0048565, in U.S. Pat. No. 9,504,780, and in International Application Publication Nos. WO2018/022158 and WO2018/201034, each of which is herein incorporated by reference in their entirety. The aspects and embodiments disclosed herein provide separation of a desired cell type, for instance a target cell, from a liquid suspension of mixed cell types including other non-target cell types. More specifically, the aspects and embodiments disclosed herein provide selective separation between cell types, without requiring the use of an affinity based capture particle.

In acoustic separation, a mixed suspension may flow through a duct that is oscillated at ultrasonic frequencies by an external mechanical oscillator. The duct may form a resonant cavity, for instance so that ultrasonic pressure waves are generated and contact the flow across the duct. For example, the ultrasonic waves may be generated at an angle relative to the flow. Ultrasonic waves may be generated in a direction substantially transverse to the flow. Cells or other particles in the suspension may experience a force from the pressure waves and migrate to nodes in the resulting pressure field. The rate at which the cells migrate generally depends on particle size, density, and compressibility. Separation may be facilitated, for example, by larger and more dense cells migrating to a pressure node, with smaller or neutrally buoyant cells migrating slowly, not migrating (substantially staying on axis), or migrating to anti-nodes. For instance, in a typical configuration separation process, the pressure node is established along the axis of the duct and certain particles may move to this pressure node axis and flow in a concentrated stream along it, while other cells may remain disperse or move to a pressure anti-node axis.

Referring again to the example application of CAR-T therapy, lymphocytes may be preferentially extracted from blood samples. The therapy may involve altering a property of the cell suspension or of a certain class of cells within the suspension, such that lymphocytes are less susceptible to acoustic energy than, for example erythrocytes and other classes of leukocytes. Therefore when a cell suspension, for example a blood sample, is passed through an acoustic separator, lymphocytes may remain in a side stream with greater abundance than undesired cells. The side stream may be collected for processing and the center stream may be discarded.

In accordance with an aspect, there is provided a method of separating target cells from non-target cells in a biofluid. More specifically, there is provided a method for selective, differential separation of a desired cell type from a biofluid comprising a suspension of mixed cell types. Target cells which may be selectively separated from the mixed cell types in the suspension include leukocytes, mononuclear cells, lymphocytes, monocytes, granulocytes, agranulocytes, macrophages, T cells, B cells, NK cells, subclasses thereof, and combinations thereof. For instance, in some embodiments, target cells are subclasses of T cells, including but not limited to CD4+, CD8+, $T_H$, $T_{CM}$, and $T_{FH}$ cells. In some embodiments, target cells are selected to be stem cells.

Non-target cells may comprise any and all cells not selected as the target cell. Non-target cells may comprise erythrocytes, platelets, granulocytes, monocytes, macrophages, leukemic cells, and leukocytes excluding the leukocytes selected as target cells. In some embodiments, the non-target cells are platelets and erythrocytes. Erythrocytes are approximately the same size as lymphocytes. In order to separate erythrocytes from lymphocytes in a biofluid, efficiency may be greatly increased by including an additive to alter or regulate at least one parameter of the biofluid. For instance, the additive may alter the aggregation potential of non-target cells and/or the density of the biofluid. According to certain embodiments, the additive is introduced in sufficient volume to regulate the density of the biofluid to be substantially similar to the density of the lymphocytes.

According to certain embodiments, target cells are separated from non-target cells to produce a target cell enriched fluid. The target cells and/or non-target cells may be live cells, frozen cells, preserved cells, or cells grown in a cell culture. The target cell enriched fluid may comprise a higher concentration of target cells, as compared to the input biofluid or the pretreated biofluid.

Generally, a biofluid, for example whole blood, comprises a high concentration of erythrocytes. To produce a target cell enriched fluid, it may be desirable to selectively deplete erythrocytes.

The method of separating target cells from non-target cells in a biofluid may further comprise providing a biofluid. In some embodiments, the biofluid may be obtained from a donor subject. The donor subject's biofluid may be subjected to down-stream processes directly, or may be collected and stored for later processing. As used herein, "directly" refers to processing of the biofluid without subjecting the biofluid to a long-term storage period. For instance, the biofluid may be processed immediately in an in-line arrangement, within minutes, or within hours. The biofluid may be stored for one day or more. In some embodiments, the biofluid is collected from a donor subject through an intraluminal line. Accordingly, the method may further comprise obtaining the biofluid from a donor subject through an intraluminal line. As used herein, an "intraluminal" line refers to a transfusion line connectable to a lumen of a subject. More specifically, an intraluminal line may be connectable to a body cavity, tubular structure, or organ in the body, such as a vein, an artery, the bladder, or intestine. For instance, a transfusion line may be connectable to the circulatory or gastrointestinal system of the subject. The intraluminal line includes, for example, intravenous lines, central venous lines, intravascular lines, intratissue lines, catheters, and transfusion lines. The intraluminal line catheter may be, for example, a peripheral indwelling catheter, an intravenous catheter, or a central venous catheter.

As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

In accordance with certain embodiments, the biofluid may be obtained from a standard blood processing device. For instance, the biofluid may be obtained from an apharesis machine. The biofluid may be directly obtained from a standard blood processing device and further processed immediately, for example in an in-line arrangement. In other embodiments, the biofluid may be obtained from a standard blood processing device and stored for one day or more before being introduced into the microfluidic separation chamber.

In some embodiments, the method further comprises selecting the biofluid from blood buffy coat, leukapheresis product, peripheral blood, whole blood, lymph fluid, synovial fluid, spinal fluid, bone marrow, ascities fluid, and combinations or subcomponents thereof. The biofluid may comprise a synthetic medium comprising a cell suspension. For instance, the biofluid may comprise a cell culture medium. In some embodiments, the biofluid may comprise a subcomponent of a biofluid. For instance, the biofluid may comprise cell enriched biofluid, cell depleted biofluid, diluted biofluid, concentrated biofluid, filtered biofluid, purified biofluid, or otherwise treated biofluid.

As used herein, leukapheresis product refers to a blood product which has undergone an apheresis separation process. The apheresis separation process may have been performed to deplete or enrich for leukocytes. Thus, the leukapheresis product may comprise leukocyte enriched apheresis product or leukocyte depleted apheresis product. In some embodiments, the leukapheresis product may comprise synthetic biofluid. In some embodiments, the leukapheresis product may be purchased from a manufacturer. In some non-limiting embodiments, the leukapheresis product is LeukoPak™ leukapheresis product (AllCells, Alameda, Calif.).

The method of separating target cells from non-target cells in a biofluid may further comprise pretreating the biofluid. In some embodiments, pretreating the biofluid comprises introducing an additive into the biofluid to alter at least one of size of the target cells, size of the non-target cells, compressibility of the biofluid, compressibility of the target cells, compressibility of the non-target cells, aggregation potential of the target cells, and aggregation potential of the non-target cells. The method may further comprise introducing an additive into the biofluid to alter at least one of density of the biofluid, density of the target cells, density of the non-target cells. The additive may be cell-friendly. For instance, in some embodiments, the concentration of additive introduced into the biofluid is generally safe for intraluminal injection into a subject. In some embodiments, the additive selected is physiologically acceptable and generally safe for intraluminal injection into a subject.

Generally, the method may comprise introducing an additive to modify the biofluid or cell chemistry, to enhance separation of target cells from non-target cells. For instance, the biofluid's electrolyte concentration (i.e. salinity or tonicity) may be adjusted, such that a desired cell type is enlarged, swollen, crenated, sphered, or rigidified in response. The desired cell type may be the target cell or the non-target cell. The change in one or more physical properties of the cell type may affect the response of the cell to the applied acoustic force within the microfluidic separation channel, enabling a differential separation between the desired cell type and other cell types within the biofluid. The method may comprise selecting the additive from the group consisting of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

The method may comprise introducing an additive to alter size or shape of the target cells or non-target cells. The cell activator may be introduced in an amount sufficient to activate a target amount of the target cells or non-target cells. In certain embodiments, a cell activator may be introduced in an amount sufficient to activate substantially all of the target cells or non-target cells. As previously mentioned, a desired cell type may become swollen, crenated, sphered, or rigidified in response to the introduction of an additive, for example, a cell activator, in the biofluid. The change in size or shape may facilitate discrimination between the cell types in the separation process. An additive may also be introduced to activate a desired cell type, whereby an activated cell type, for example, T cell or B cell, may be larger than a non-activated cell of the same type, for example, T cell or B cell. Thus, natural morphological changes due to biochemically induced activation or the natural cell cycle may be exploited to separate target cells from non-target cells.

In accordance with certain exemplary embodiments, the additive may comprise an activation reagent selected from CpG oligodeoxynucleotides (CpG ODN), a soluble CD3 antibody, a bead coated with humanized CD3 and CD28 agonist antibodies, and Interleukin 2 (IL-2). The CpG ODN may be of any class, (for example, Class A, Class B, Class C, Class P, or Class S) and may have an optimal sequence selected to activate a desired cell type. In some embodiments, CpG ODN may be introduced to activate B-lymphocytes (B cells). Beads coated with humanized CD3 and CD28 agonist antibodies, for example, TransAct™ beads (distributed by Miltenyi Biotec, Bergisch Gladbach, Germany) may be introduced to activate cells. For instance, T cell TransAct™ beads may be introduced to activate T-lymphocytes (T cells). Soluble CD3 antibodies may be introduced to activate cells, for example, T-lymphocytes. Additionally, regulatory proteins, for example, IL-2, may be introduced to activate cells, for example, T-lymphocytes. Other regulatory proteins or cell activation reagents may be used.

The method may comprise introducing an additive to alter sodium or ion concentration of the biofluid. For instance, a concentrated sodium chloride solution may be introduced to crenate and/or shrink erythrocytes and other non-target cells by osmosis. Without wishing to be bound by a particular theory, it is believed that hemoglobin contained within erythrocytes will effectuate an increase in density simultaneously with a decrease in volume of the cell. Thus, it may be possible to selectively increase the density of erythrocytes by decreasing their size, to promote an enhanced separation of target cells from non-target erythrocytes.

In some embodiments, the method comprises introducing an additive to alter compressibility of the biofluid, target cells, or non-target cells. For instance, detergents and/or surfactants may be added to alter cell membrane mechanics, such that desired cell types undergo a change in compressibility. In some embodiments, detergents or surfactants alter the cell membrane, such that desired cell types are more susceptible to changes in ion concentration in the biofluid. For instance, non-ionic detergents may comprise the Tween™ family of detergents, Brij-35™ detergents, or the Pluronic™ family of detergents. Such detergents are known to affect membrane permeability and cellular biomechanics at very low concentrations of less than 0.05% weight/volume fraction of detergent. Thus, by adding certain detergents, it may be possible to differentially affect the cellular mechanical properties of cell density, shape, size or ionic content in order to promote an enhanced separation of target cells from non-target cells.

An additive may be introduced into the biofluid to alter aggregation potential of the target cells or the non-target cells. As used herein, "aggregation potential" refers to the mechanism by which a desired cell type aggregates, agglutinates, adheres, or forms a complex with like cells. In some embodiments, the aggregation potential refers to a desired cell type's ability to aggregate with cells of a different cell type. For instance, an additive may be introduced to alter or regulate the aggregation potential of erythrocytes or platelets. Generally, many biofluids comprise a high concentration of erythrocytes and/or platelets. By aggregating the erythrocytes and/or platelets, a more efficient separation from other cells may be achieved.

In some embodiments, the aggregation potential is altered or regulated by an additive that prohibits a desired cell type from binding, aggregating, agglutinating, adhering, or forming a complex with a like or different cell type. For instance, the aggregation potential may be altered or reduced by an anti-coagulant. In other embodiments, the aggregation potential may be altered, enhanced, or regulated by a cell aggregator. As used herein, a "cell aggregator" refers to an additive that may bind, aggregate, adhere, agglutinate or form a complex with a desired cell type. A "cell aggregator" may also refer to an additive that may cause a desired cell type to bind, aggregate, adhere, agglutinate, or form a complex with like or different cell types. The cell aggregator may cause cells to aggregate by activating natural biochemical pathways, by altering cell mechanics, or by reducing or screening electrostatic barriers between cells in the pretreated biofluid.

In some embodiments, the method further comprises selecting the cell aggregator to be a long-chain polysaccharide. Long-chain polysaccharides include, but are not limited to, dextran, polysucrose, hetastarch (hydroxyethyl starch), and Ficoll™ media, distributed by GE Healthcare (Chicago, Ill.). The long-chain polysaccharide may have a molecular weight between about 100 kD and about 500 kD. In some embodiments, the long-chain polysaccharide has a molecular weight between about 250 kD and about 500 kD, between about 200 kD and about 400 kD, between about 300 kD and about 400 kD. The long-chain polysaccharide may have a molecular weight of about 100 kD, about 200 kD, about 250 kD, about 300 kD, about 400 kD, and about 500 kD. In some embodiments, the cell aggregator comprises a long-chain polysaccharide present at a concentration of between about 0.5% (w/v) and about 25% (w/v). In some embodiments, the cell aggregator comprises a long-chain polysaccharide present at a concentration of between about 1.0% (w/v) and about 20% (w/v), between about 5.0% (w/v) and about 15% (w/v), between about 8.0% (w/v) and about 12% (w/v). For instance, the cell aggregator may comprise a long-chain polysaccharide present at about 0.5% (w/v), about 1.0% (w/v), about 2.0% (w/v), about 5.0% (w/v), about 8.0% (w/v), about 10% (w/v), about 12% (w/v), about 15% (w/v), about 20% (w/v), about 24% (w/v), and about 25% (w/v).

In some embodiments, the method further comprises selecting the cell aggregator to be a platelet aggregator or a cell adhesion molecule (CAM). The CAM may be released or obtainable from an activated platelet granule. Such CAMs aggregate platelets by known natural mechanisms. Platelet activation may induce the platelet to release granules and expose the contents of platelet granules on the outside of the cell. CAMs may then promote platelet aggregation through platelet-fibrin and platelet-platelet binding. CAMs may be released from an activated platelet granule by biochemically inducing their release, for example through activation by addition of thrombin, Type II collagen or adenosine diphosphate, or by introducing natural or synthetic CAMs obtained from a distributor into the biofluid. The CAMs released or obtainable from an activated platelet granule may include, but are not limited to, P-selectin and von Willebrand factor. Platelet activators include, but are not limited to, adenosine diphosphate, thrombin, Type II collagen, and ristocetin.

Figure 15:
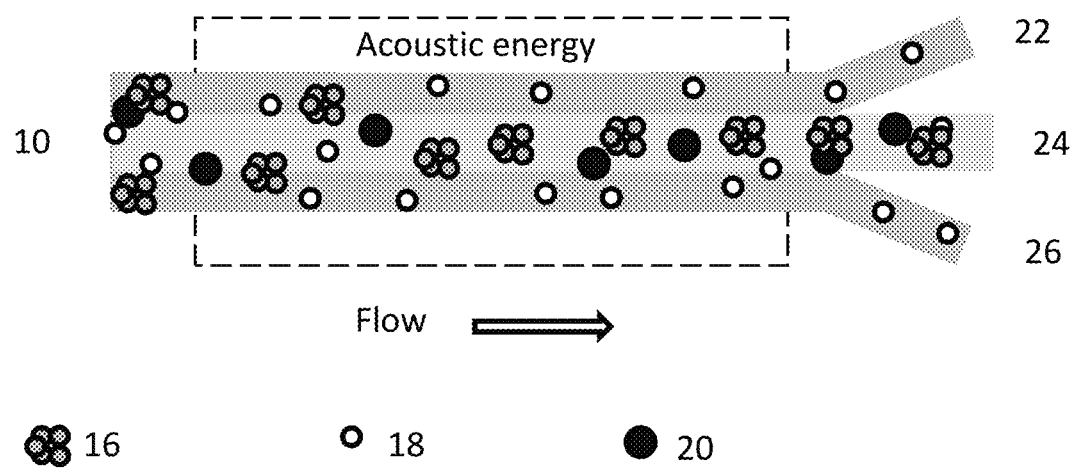
FIG. 15 is a schematic drawing of an alternate microfluidic separation channel, according to another embodiment.

As shown in the exemplary concept schematic drawing of FIG. 15, applied acoustic energy may move cell aggregates 16 to a central waste stream 24 together with larger and more dense cells 20. Mid-sized target cells 18 may be collected through collection streams 22 and 26.

An additive may be introduced into the biofluid to alter density of the biofluid. In some embodiments, the additive is selected from a density gradient medium, a density additive, and combinations thereof. Density gradient media is a media for cell isolation, generally used in the practice of centrifugal separation. Density gradient media are well known in the art and include, for example, ACCUSPIN™ media, Histodenz™ media, OptiPrep™ media, and Histopaque® media distributed by Sigma-Aldrich (St. Louis, Mo.), Ficoll-Paque™ media and Percoll™ media distributed by GE Healthcare (Chicago, Ill.), RosetteSep™ media and Lymphoprep™ media distributed by STEMCELL Technologies (Vancouver, Canada). The list of density gradient media is merely exemplary and non-exhaustive.

A density additive may comprise a reagent having a different density than the biofluid, or configured to regulate or alter the density of the biofluid. For instance, the density additive may comprise pure water, deionized water, a salt, a saline buffer solution, or a nonionic iodinated compound. Nonionic iodinated compounds include, but are not limited to, diatrizoic acid, meglumine diatrizoate, and iodixanol. According to certain embodiments, the density additive is selected to be cell-friendly, such that it does not increase osmolarity of the biofluid to a degree that would be harmful to the cells. For instance, the density additive may be selected to not comprise cesium chloride or sucrose.

In some embodiments, the additive is introduced to alter or regulate the density of the biofluid to be within a range of the density of the target cells or non-target cells. For example, the density may be regulated such that target cells approach neutral acoustic buoyancy in the biofluid, reducing the acoustic force acting on them, as compared to the force acting on the non-target cells. In other embodiments, the density may be regulated such that the biofluid density is slightly different than the average density of the target cells, for example, between about 0.01 g/mL and about 0.05 g/mL less or more than the average density of the target cells, for example, about 0.01 g/mL, about 0.02 g/mL, about 0.03 g/mL, about 0.04 g/mL, or about 0.05 g/mL less or more than the average density of the target cells. The density of the biofluid may be regulated to a density of between about 1.00 g/mL and about 1.15 g/mL. In some embodiments, the density of the biofluid is regulated to a density of between about 1.00 g/mL and about 1.10 g/mL, between about 1.10 g/mL and about 1.15 g/mL, between about 1.02 g/mL and about 1.09 g/mL, between about 1.03 g/mL and about 1.08 g/mL, between about 1.04 g/mL and about 1.07 g/mL, and between about 1.045 g/mL and about 1.065 g/mL. Specifically, the density of the biofluid may be regulated or altered to a density of about 1.00 g/mL, about 1.01 g/mL, about 1.02 g/mL, about 1.03 g/mL, about 1.04 g/mL, about 1.05 g/mL, about 1.06 g/mL, about 1.07 g/mL, about 1.08 g/mL, about 1.09 g/mL, about 1.10 g/mL, about 1.12 g/mL, and about 1.15 g/mL.

Pretreating the biofluid may further comprise introducing an additive to alter density of the target cells or non-target cells. The additive may be introduced to alter or regulate the density of biofluid and cells to be within a range of each other, for instance to make the cells approach neutral acoustic buoyancy within the fluid. A diluent, salt, or saline solution may be introduced to alter or regulate the density of target cells or non-target cells to illicit a certain response from a desired cell type or to have a density within a range of the density of the biofluid. For instance, sodium or an ion concentration may be reduced, for example by dilution with deionized water, to swell erythrocytes by osmosis while lymphocytes use known natural mechanisms to regulate their size, increasing size discrimination between the two cell types. In another non-limiting example, leukemic cells swell more readily than healthy lymphocytes, and the additive may facilitate removal of the leukemic cells.

The method may comprise introducing an additive to alter both density of the biofluid and aggregation potential of the non-target cells. In some embodiments, the combination of a density additive and a cell aggregator produces a synergistic effect, whereby the method produces a more efficient separation of target cells from non-target cells and a higher concentration of target cells in the target cell enriched fluid than would be expected from the combination of both effects. For instance, in a method of separating lymphocytes from other leukocytes and erythrocytes, an additive or a combination of additives may be introduced to alter the density of the biofluid and to aggregate erythrocytes. The density additive may enhance the separation of the target cell, or lymphocytes in this example, from the non-target cells (for example, leukocytes), while the cell aggregator may effectively increase the acoustic scattering radius of the non-target cells to enhanced separation of the non-target cells over the lymphocyte or other target cells. The individual additives, when used separately, may not provide sufficient separation of lymphocytes from non-target cells, but the combination may promote an enhanced effective differential separation of target cells from non-target cells.

In some embodiments the additive may further comprise affinity based capture particles. Generally, the affinity based particles are safe for intraluminal injection into a subject. For instance, the additive may comprise biochemical moieties, such as antibodies, that bind target cells or non-target cells. The cell aggregator may comprise a solution comprising antibodies that bind and aggregate target cells or non-target cells. In some embodiments, the antibodies bind and aggregate a desired cell type. The additive may comprise emulsion droplets, gel particles, or lipid encapsulated oil vesicles. In some embodiments, the affinity based capture particle is safe for intraluminal injection.

The affinity based capture particle may be engineered to be "anti-focusing" or "positively focusing" by designing it with low density or high density. The low density "anti-focusing" capture particle may experience acoustophoretic forces in the opposite direction as the target cells or non-target cells. The high density "anti-focusing" capture particle may experience migration to the pressure anti-node, while target cells or non-target cells migrate toward the pressure node. In some embodiments, an acoustic analog to magnetic separation may comprise "positively focusing" capture particles. For instance, a "positively focusing" capture particle may be used to trap a desired cell type, such that selected cells remain held in the separation channel, while other cells flow through. The held cell type may be released at a later time. In some embodiments, a large capture particle molecule may bind to many points on the surface of a desired cell type, and may alter the acoustophoretic force exhibited on the particle by changing its effective diameter.

In some embodiments, the additive may further comprise one or more metallic nanoparticles. The metallic nanoparticles may include, for example, gold or iron nanoparticles. While not wishing to be bound by any particular theory, it is believed that certain cell types may ingest or phagocytose the metallic nanoparticles, while other cell types will not. Alternatively, certain cell types may ingest or phagocytose the metallic nanoparticles at a faster rate than other cell types. The cells that ingest or phagocytose the metallic nanoparticles may have a different density and/or size, thereby making them separable from other cell types by the methods disclosed herein.

The method of separating target cells from non-target cells may further comprise flowing biofluid into an inlet of a microfluidic separation channel. For instance, the method may comprise flowing the pretreated biofluid into the microfluidic separation channel. The biofluid may have a flow rate of between about 0.03 mL/min to about 0.5 mL/min. In some embodiments, the biofluid may have a flow rate through the microfluidic separation channel of between about 0.05 mL/min to about 0.4 mL/min, about 0.1 mL/min to about 0.3 mL/min. The biofluid may have a flow rate through the microfluidic separation channel of about 0.03 mL/min, 0.05 mL/min, 0.08 mL/min, 0.1 mL/min, 0.2 mL/min, 0.3 mL/min, 0.4 mL/min, 0.5 mL/min, or any range therebetween.

The method may further comprise applying acoustic energy to the microfluidic separation channel. In some embodiments, the acoustic energy is applied in the form of an acoustic wave. The acoustic wave may be applied at an angle relative to the flow of fluid through the separation channel. The angle and magnitude of the acoustic wave may be engineered based on size of the device, size of the channel, or flow rate of fluid through the channel. In some embodiments, the acoustic energy may be applied in a direction substantially transverse to the biofluid flow through the microfluidic separation channel. The acoustic wave may be a standing acoustic wave. In some embodiments, the acoustic energy may be applied to the microfluidic separation channel continuously. The continuous application of acoustic energy may allow for a greater efficiency of separation. In alternate embodiments, the acoustic energy may be applied to the microfluidic separation channel intermittently or on a timed schedule. The intermittent energy application may allow for cells to move freely through the channel if there is a blockage.

The applied acoustic energy may act on the cells and particles within the biofluid to drive them according to size, density, and/or compressibility. In some embodiments, the method may comprise accumulating target cells within a primary stream along the separation channel. In some embodiments, the method may comprise accumulating non-target cells within a secondary stream along the separation channel. The accumulation of a cell type within a desired stream along the separation channel may be engineered by adjusting parameters such as wavelength, frequency, amplitude, power level, or other modulation of the applied acoustic energy.

Depending on the target cells or non-target cells selected according to the method, one class of cells may accumulate in response to a pressure node or anti-node generated by the acoustic energy. For instance, target cells may accumulate within a primary stream in response to a pressure node, and non-target cells may accumulate within a secondary stream in response to a pressure anti-node. Generally, particles, including cells, will be driven by the acoustic energy in response to their contrast factor. Particles may migrate at a rate which is proportional to the magnitude and sign of their contrast factors. In some embodiments, particles with a positive contrast factor are driven to pressure nodes, while particles with a negative contrast factor are driven to pressure anti-nodes. Particles with a greater magnitude contrast factor are generally driven at a faster rate than particles with a lesser magnitude contrast factor.

The rate at which cells are driven in response to their acoustic energy generally depends on particle size, density, and compressibility. Briefly, the contrast factor is based on the bulk modulus (K) and density (ρ) of a particle, here of the cells. When suspended in a fluid, the contrast factor (φ) for the cells is calculated with the below equation:

$$\varphi = \frac{5\rho - 2 \cdot 1.02}{2\rho + 1.02} + \frac{2.2}{K}$$

In some embodiments, the method of separating target cells from non-target cells in a biofluid comprises collecting the at least one primary stream comprising the target cells. Generally, the biofluid entering the microfluidic separation channel is a well-mixed primary stream, comprising desegregated target cells and non-target cells. Upon experiencing acoustic energy, target cells and non-target cells may generally accumulate into fractions of the general stream of biofluid. The fraction or fractions of biofluid flowing through the microfluidic separation channel selectively enriched in target cells are defined as the primary stream. There may be more than one fraction of biofluid within the microfluidic separation channel enriched in target cells. For instance, target cells may be driven to a pressure node at the center of the channel in one embodiment, and target cells may be driven to the pressure anti-nodes at the periphery of the channel in an alternate embodiment. The location of pressure nodes and anti-nodes within the channel may be designed by positioning the acoustic energy or by selecting frequency and wavelength of the acoustic waves. The primary stream comprising target cells may be collected for storage, immediate use, transfusion into a patient, or for research. In certain embodiments, where the method is designed to create a target cell depleted fluid, the primary stream comprising target cells may be discarded as waste.

Similarly, in some embodiments, the method of separating target cells from non-target cells comprises collecting the at least one secondary stream comprising non-target cells. The fraction or fractions within the biofluid selectively depleted in target cells, and selectively enriched in non-target cells are defined as the secondary stream. In certain embodiments, the target cells and non-target cells have opposing contrast factors. With opposing contrast factors, the target cells and non-target cells may be driven in opposite directions, or one may be driven away from the general stream, for example to the center or the periphery of the channel. In other embodiments, the target cells and non-target cells have contrast factors of a different magnitude, but the same sign. In these embodiments, one class of cells may be driven away at a faster rate than the other, defining the primary and secondary streams. The secondary stream may be collected for storage, for further research, or to be discarded as waste. Where the method is designed to deplete a biofluid of the target cells, the secondary stream may be collected for later use or for transfusion into a patient. The method may comprise collecting the primary stream comprising target cells and further comprise separately collecting the at least one secondary stream comprising the non-target cells.

According to certain embodiments, a target cell enriched or target cell depleted fluid may be post-treated and delivered to a recipient subject. For instance, the primary stream may be post-treated and delivered to a recipient subject. Post-treating a fluid may comprise a process such as washing, separating, concentrating, diluting, heating, purifying, or filtering capable of removing toxins, contaminants, or harmful chemical compounds from the fluid. In general, a fluid is post-treated to produce a physiologically acceptable fluid that may be directly delivered to a recipient subject, for example via an intraluminal line as previously described. The post-treated fluid may be stored for delivery to a recipient subject at a later time.

In some embodiments, the target cell enriched or target cell depleted fluid is post-treated to produce a therapeutic fluid. Post-treating the fluid may comprise viral transduction, gene transfer, or gene editing of the target cells to produce a therapeutic, physiologically acceptable fluid for delivery to a recipient subject, as previously described.

In some embodiments, the recipient subject is the same as the donor subject. In other embodiments, the donor subject and the recipient subject are not the same. The donor subject and the recipient subject may generally be physiologically compatible.

The method may be performed in line such that the biofluid is collected from a subject and directly pretreated, target cells are separated from non-target cells in the biofluid by a method as described herein to produce a target cell enriched fluid, the fluid enriched in target cells may be post-treated, and the post-treated fluid may be directly delivered back to the subject. In some embodiments, the method is performed essentially as previously discussed, however the target cells are separated from non-target cells to produce a target cell depleted fluid, which may be post-treated and delivered back to the subject.

According to certain embodiments, the method further comprises flowing a second fluid adjacent to the biofluid into an inlet of the microfluidic separation channel. The inlet may be an inlet separate from the biofluid inlet of the microfluidic separation channel. The biofluid and the second fluid may flow through the separation channel in substantially parallel form. For instance, both fluids may flow through the separation channel at opposite peripheries of the channel, the second fluid may flow through both peripheries of the channel, or the second fluid may flow in the center of the channel. The biofluid and the second fluid may flow through the separation channel in substantially laminar form. As used herein, substantially laminar flow includes substantially ordered flow. Laminar flow may have a Reynolds number (Re) less than about 2100. In certain embodiments, laminar flow has a Reynolds number (Re) less than about 4000.

In certain embodiments, the second fluid is an inert fluid that may comprise water, deionized water, or phosphate buffered saline (PBS). The second fluid may have its density adjusted with a density gradient medium or density additive, independently from the pre-treated biofluid. The applied acoustic energy may drive target or non-target cells from the biofluid into the essentially parallel flowing second fluid initially comprising no cells, such that the second fluid, now comprising selectively separated cells, may exit the microfluidic separation channel through a separate outlet. Where the target cells are driven into the second fluid, the second fluid comprising target cells is essentially the primary stream. Conversely, where the non-target cells are driven into the second fluid, the second fluid is essentially the secondary stream.

According to certain embodiments, the methods described herein may be performed in a staged separation or in series. Specifically a target cell enriched fluid or a target cell depleted fluid may be further processed by pretreating with an additive, flowing through a second microfluidic separation channel, and applying acoustic energy. The additive introduced into the fluid in the downstream operation may be the same or a different additive as the one introduced into the biofluid in the first pass separation process. Additionally, the target cells selected in the first pass process may be the same or different as those selected in the second pass process. As a non-limiting example, a biofluid may be pretreated and flowed through a microfluidic separation channel to produce a platelet depleted fluid. The output platelet depleted fluid may further be flowed through a second microfluidic separation channel to remove neutrophils and/or monocytes. As another non-limiting example a biofluid may be flowed through a microfluidic separation channel to produce lymphocyte enriched fluid. The lymphocyte enriched fluid may be flowed through a second microfluidic separation channel to produce a further lymphocyte enriched fluid.

In some embodiments, the first pass target cell enriched or target cell depleted fluid is recycled and reintroduced into the biofluid or into the pretreated biofluid to flow through the microfluidic separation channel as a blend.

According to certain embodiments, the method further comprises dosing the at least one primary stream with a reagent to produce a dosed suspension. The at least one primary stream may be a target cell enriched fluid. The reagent may be selected from an antigen or activation reagent configured to biochemically induce cell activation. The biochemically induced activation may allow for selection of subclasses of types of cells, for instance lymphocytes or T cells, by exploiting the morphological changes of activated cells. In some instances, activated cells may be larger than non-activated cells and cell size may vary throughout the cell cycle. The difference in size may allow for differential separation with acoustic energy.

The method may further comprise flowing the target cell enriched fluid through a second microfluidic separation channel or through microfluidic separation channels arranged in series and applying acoustic energy to each separation channel. The dosed suspension may allow for selection of target cells at a certain stage of the cell cycle.

For instance, in some embodiments of the method, the target cells in the primary stream may be lymphocytes and the method may further comprise separating activated lymphocytes from non-activated lymphocytes in the primary stream. The method may further comprise dosing the lymphocyte enriched fluid with a reagent to produce the dosed suspension, flowing the dosed suspension into an inlet of a second microfluidic separation channel, and applying acoustic energy to the second microfluidic separation channel. Activated lymphocytes may accumulate within at least one primary stream along the second separation channel and non-activated lymphocytes may accumulate within at least one secondary stream along the second separation channel.

In accordance with another aspect, there is provided a system for microfluidic cell separation. The system may be configured to separate target cells from non-target cells in a biofluid. In some embodiments, the system comprises at least one microfluidic separation channel comprising at least one inlet and at least one outlet. The at least one outlet may be a branched outlet, branching in a direction substantially away from the separation channel. In some embodiments, the microfluidic separation channel comprises a first outlet and a second outlet. The at least one inlet may be configured to receive biofluid and the at least one outlet may be configured to discharge the biofluid that has been subjected to acoustic energy. As the fluid flows through the microfluidic separation channel, it may be subjected to acoustic energy that drives the target cells and/or non-target cells towards pressure nodes and anti-nodes within the channel. In some embodiments, the first outlet is configured to discharge target cell enriched fluid and the second outlet is configured to discharge target cell depleted fluid.

The microfluidic separation channel may be formed of rigid materials. The rigid materials may have a high acoustic contrast with the biofluid. In alternate embodiments, the microfluidic separation channel may be formed of relatively elastic materials. The more elastic materials may have a lower acoustic contrast with the biofluid, however they may form good acoustic resonators that provide low acoustic impedance and provide relatively little wave energy loss in wave transfer. The materials to form the microfluidic separation channel may include silicon, glass, metals, thermoplastics, and combinations thereof. In some embodiments, the microfluidic separation channel may be formed of a thermoplastic material. The thermoplastic microfluidic separation channel may be small, disposable, relatively safer to handle than, for example, the glass or metal separation channels, and relatively less expensive to manufacture than the silicon, glass, or metal separation channels. In some embodiments, the thermoplastic microfluidic separation channels are manufactured by injection molding. The thermoplastic material may comprise polystyrene, acrylic (polymethyl methacrylate), polysulfone, polycarbonate, polyethylene, polypropylene, cyclic olefin copolymer, silicone, liquid crystal polymer, polyvinylidene fluoride, and combinations thereof. The microfluidic separation channel may be disposable.

In some embodiments, the microfluidic separation channel has a channel width of between about 0.2 mm to about 0.8 mm. The microfluidic separation channel may be about 0.2 mm, about 0.3 mm, about 0.4 mm, about 0.5 mm, about 0.6 mm, about 0.7 mm, or about 0.8 mm wide. In some embodiments, the microfluidic separation channel is between about 15 mm and about 35 mm long. The microfluidic separation channel may be about 15 mm, about 20 mm, about 25 mm, about 30 mm, or about 35 mm long. The microfluidic separation channel width may be correlated to the acoustic wave wavelength, such that each channel contains a pressure-node and/or pressure anti-node generated by the acoustic energy.

The system may further comprise a source of biofluid in fluid communication with the microfluidic separation channel. The source of the biofluid may be a vessel or chamber in fluid communication with the at least one inlet of the microfluidic separation channel, configured to deliver biofluid to the separation channel. The source of the biofluid may be a mixing chamber configured to receive an additive or a second fluid to be introduced into the biofluid prior to flowing the biofluid through the microfluidic separation channel. The source of the biofluid may be heated, cooled, or mixed.

In some embodiments, the source of the biofluid is fluidly connected downstream of an intraluminal line, and configured to receive biofluid directly from a donor subject. The source of the biofluid may further be fluidly connected downstream to a biofluid sample, for instance a sample collected in a bag, vessel, tank, or other chamber.

In some embodiments, the system comprises a source of additive in fluid communication with the source of the biofluid, configured to introduce at least one additive into the biofluid. The additive contained in the source of the biofluid may be an additive capable of altering or regulating at least one of size of the target cells, size of the non-target cells, compressibility of the biofluid, compressibility of the target cells, compressibility of the non-target cells, aggregation potential of the target cells, and aggregation potential of the non-target cells, as previously discussed. The additive may further be capable of altering or regulating at least one of density of the biofluid, density of the target cells, density of the non-target cells. The source of the additive may be a chamber, vessel, or tank comprising the additive. In some embodiments, the system comprises more than one source of an additive, each source configured to introduce a separate additive into the biofluid. In some embodiments, the source of the additive may be heated, cooled, or comprise a mixer.

The system may further comprise at least one acoustic transducer coupled to a wall of the microfluidic separation channel. The acoustic transducer may be positioned to apply a standing acoustic wave transverse to the microfluidic separation channel. In some embodiments, the acoustic transducer is capable of emitting acoustic energy that drives cells and/or particles to a pressure node or anti-node. The acoustic transducer may comprise a piezoelectric vibrating element configured to emit acoustic energy. The denser and larger particles and cells may migrate towards the center of the separation channel in response to the acoustic energy emitted by the piezoelectric transducer. In some embodiments, the acoustic transducer is configured to emit acoustic energy between about 1.0 MHz and about 4.0 MHz. For instance, the acoustic transducer may emit acoustic energy between about 1.5 MHz and about 3.5 MHz or between about 1.0 MHz and about 2.0 MHz. The acoustic transducer may be configured to provide standing acoustic waves having a wavelength that is twice as long as the microfluidic separation channel width.

The microfluidic separation channel may further comprise one or more heat sinks configured to dissipate heat generated by the acoustic transducer. The heat sink may be configured to dissipate enough heat from the acoustic transducer to prevent the transducer from warming fluids flowing through the separation channel. In some embodiments, the heat sinks comprise thermoelectric coolers. In some embodiments, the system includes fluidic lines that flow into the heat sink to provide fluidic cooling to the heat sink.

Systems that comprise more than one microfluidic separation channel may comprise one acoustic transducer coupled to each microfluidic separation channel or one or more acoustic transducers coupled to a collection of microfluidic separation channels.

In some embodiments, the system comprises at least two microfluidic separation channels. The at least two microfluidic separation channels may be arranged in a parallel arrangement downstream of the source of the biofluid. In such embodiments, the system may further comprise a manifold configured to distribute biofluid to the at least two microfluidic separation channels. The manifold may be configured to receive a biofluid or pretreated biofluid sample and evenly distribute the sample to downstream microfluidic separation channels. In some embodiments, the manifold may be configured to continuously receive and distribute fluid, and in other embodiments the manifold may be configured to receive and distribute fluid in batches. The manifold configured to receive and distribute fluid in batches may be on a regular timer or may distribute fluid batches as it receives sufficient fluid.

In some embodiments, the manifold is configured to distribute the biofluid in response to the input biofluid load on the system. In some embodiments, the input biofluid load comprises between about 1 mL to about 1 L of fluid. In some embodiments, the input biofluid load on the system may have a flow rate of between about 0.1 mL/min to about 10 mL/min. Each microfluidic separation channel may be configured to receive flow rates of between about 0.1 mL/min to about 0.5 mL/min. The system may further comprise at least one sensor configured to measure an input biofluid load on the system. The input biofluid load sensor may be in electrical communication with the manifold, such that the manifold may distribute the biofluid to the two or more microfluidic separation channels in response to the measurement of the input biofluid load received from the input biofluid load sensor.

In some embodiments, the system further comprises at least one sensor configured to measure at least one parameter of the input biofluid. For instance, the biofluid sensor may be configured to measure at least one of density of the biofluid, HCT % of the biofluid, concentration of target cells, or concentration of non-target cells in the biofluid. In some embodiments, the biofluid sensor is configured to measure optical transmission or absorption of the biofluid at a predetermined optical wavelength. The at least one biofluid sensor may be positioned at the system input and configured to measure parameters from the input biofluid load, or may be positioned within the source of the biofluid and configured to measure parameters from the biofluid or pretreated biofluid. The system may further comprise a control module in electrical communication with the biofluid sensor. The control module may further be in electrical communication with the source of additive, and configured to introduce a predetermined volume of the additive into the biofluid in response to the measurement of the at least one parameter of the input biofluid. In particular, the control module may be configured to introduce the additive responsive to the measurement of the parameter being outside tolerance of a target value. The target value may be a value sufficient to indicate separation of all or substantially of the target cells from non-target cells. In some embodiments, the target value may be a value sufficient to indicate separation of at least 70%, at least 80%, at least 90%, at least 95%, or at least 99% of the target cells from non-target cells. The threshold may be within about 10%, about 5%, about 3%, about 2%, about 1%, or about 0.5% of the target value.

In certain embodiments the additive is capable of altering or regulating at least one of density of the biofluid, density of the target cells, density of the non-target cells, and the predetermined volume of the additive is determined to alter or regulate the biofluid to have a desired density or concentration of target cells or non-target cells. For instance, the predetermined volume of the additive may be determined to allow target cells or non-target cells to approach neutral acoustic buoyancy in the biofluid. In some embodiments, the predetermined volume of the additive is determined to alter or regulate the density of the biofluid to a density of between about 1.00 g/mL and about 1.15 g/mL or to density ranges or values within this range, as previously discussed.

In some embodiments, the additive is capable of altering or regulating at least one of HCT % of the biofluid, concentration of the target cells, or concentration of the non-target cells, and the predetermined volume of the additive is determined to alter or regulate the HCT % of the biofluid to be less than about 10%. For instance, the predetermined volume of the additive may be determined to alter or regulate the HCT % of the biofluid to be less than about 30%, less than about 25%, less than about 20%, less than about 15%, less than about 10%, or less than about 5%.

According to certain embodiments, the system further comprises at least one sensor configured to measure a parameter of an output suspension. The output suspension may be target cell enriched fluid or target cell depleted fluid exiting the microfluidic separation channel through the at least one outlet, or product or waste exiting the system. The sensors may measure at least one of HCT %, concentration of target cells, or concentration of non-target cells in the output suspension. In some embodiments, the sensors may measure at least one of density of the output suspension, density of the target cells, density of the non-target cells, size of the target cells, size of the non-target cells, compressibility of the output suspension, compressibility of the target cells, compressibility of the non-target cells, and concentration of the additive in the output suspension. In some embodiments, the sensors may measure optical transmission or absorption of the output suspension at a predetermined wavelength.

The system may further comprise a control module in electrical communication with the output suspension sensor. The control module may be in electrical communication with the acoustic transducer, and configured to alter or regulate at least one input parameter of the acoustic transducer. For instance, the control module may alter or regulate the power, voltage, or frequency delivered to the acoustic transducer in response to a measurement of a parameter of the output suspension. The control module may further shut on or off the acoustic transducer in response to a measurement of a parameter of the output suspension. For instance, the control module may act in response to a measurement of HCT %, concentration of target cells, or concentration of non-target cells in the output suspension. The control module in communication with the output suspension sensor may be the same or different from the control module in communication with the biofluid sensor.

In some embodiments, any control module may be designed to act in response to a measurement from any sensor within the system. For instance, the control module configured to introduce a predetermined volume of additive into the biofluid may further be in electrical communication with the output suspension sensor or input biofluid load sensor, and configured to act in response to a measurement received therefrom. In another embodiment, the control module configured to be in electrical communication with the acoustic transducer may also be in electrical communication with other sensors and configured to act in response to a measurement received from the biofluid load sensor or the biofluid sensor.

In some embodiments, the predetermined volume of the additive or the power, voltage or frequency delivered to the acoustic transducer are controlled to regulate the HCT % of the output suspension. For instance, the system may be controlled to provide an output suspension having a desired HCT % of less than about 20%, less than about 10%, or less than about 1%. In some embodiments, the HCT % of the output suspension is controlled to be less than about 10%, less than about 9%, less than about 8%, less than about 7%, less than about 6%, less than about 5%, less than about 4%, less than about 3%, less than about 2%, or less than about 1%. The desired output suspension HCT % will depend on the exact biofluid flowed through the system and the input biofluid HCT %. For example, if the input biofluid is whole blood having HCT % of 45%, the system may be controlled to provide an output suspension having HCT % of about 5%.

The system may further comprise a source of a second fluid in fluid communication with the at least one inlet of the at least one microfluidic separation channel. The source of the second fluid may be a vessel, tank, or chamber in fluid communication with the microfluidic separation channel, the source of the biofluid, or a line connecting the source of the biofluid with the at least one inlet of the microfluidic separation channel. The source of the second fluid may be configured to introduce the second fluid into the biofluid. In some embodiments, the biofluid and the second fluid flow in substantially parallel, substantially laminar flow, as previously discussed. The second fluid may be any fluid, as previously discussed.

In some embodiments, the system may further comprise a first and second collection channel in fluid communication with the at least one outlet of the microfluidic separation channel. The collection channel may be a fluid line configured to deliver output suspension to a vessel, recycle line, or fluidly connectable with an intraluminal line configured to deliver output suspension to a subject. A collection vessel may be in fluid communication with the first or second collection channel. The collection vessel may be used to store, freeze, heat, or otherwise keep output suspension.

According to certain embodiments, the system further comprises a recycle line. In some embodiments, the recycle line is a line or channel configured to deliver output suspension back to the source of the biofluid for a second pass separation. The recycle line may be configured to deliver output suspension back to the at least one inlet of the microfluidic separation channel. The output suspension that is recycled may be target cell enriched fluid or target cell depleted fluid.

In some embodiments, the system comprises a post-treatment chamber. The post-treatment chamber may be configured to post-treat output suspension to produce a post-treated fluid, physiologically acceptable fluid, or therapeutic fluid, as previously described.

The system may comprise one or more pumps to direct the biofluid through the system. The one or more pumps may be an infusion pump configured to generate sufficient pressure to force the biofluid through the system. In some embodiments, the pump generates sufficient pressure to introduce the output suspension into the recipient subject through the intraluminal line.

The system may be connectable to more than one intraluminal line to produce an in-line system for separation of cells. For instance, the system may be connectable to an intraluminal line configured to extract biofluid from a donor subject and deliver it to the source of the biofluid for processing. The system may be connectable to an intraluminal line configured to deliver an output suspension, for example target cell enriched fluid or target cell depleted fluid, to the recipient subject. In some embodiments, the recipient subject may be the same as the donor subject, and the biofluid processing is performed in line and in real time.

In some embodiments, the system comprises more than one microfluidic separation channel arranged in series. The more than one microfluidic channel in series may be configured to separate target cells from non-target cells in consecutive separation channels to produce a fluid with high target cell purity. In some embodiments, the more than one microfluidic separation channel in series is configured to deliver target cell enriched fluid to downstream microfluidic separation channels. In alternate embodiments, the more than one microfluidic separation channel in series is configured to deliver target cell depleted fluid to downstream microfluidic separation channels. In some embodiments, the microfluidic separation channels in series are stacked to process relatively larger volumes of biofluid. The stacked configuration allows branched outlets of the separation channel to be easily connectable to branched inlets of a downstream separation channel.

In accordance with another aspect, there is provided a kit for separation of target cells from non-target cells. The kit may comprise at least one microfluidic separation channel connected to an acoustic transducer, a source of an additive fluidly connectable to the at least one inlet of the microfluidic separation channel, and instructions for use. The at least one microfluidic separation channel may be configured to separate target cells from non-target cells, as previously described herein. The source of the additive may be a vessel, chamber, or channel, as previously discussed herein and may comprise at least one additive, as previously discussed herein. The kit may further comprise any component of the system described herein, connectable to the microfluidic separation channel. For instance, according to certain embodiments, the kit may further comprise a collection channel, a collection vessel, a manifold system, a sensor, a control module, an intraluminal line, a pump, a post-treatment chamber, or fluid lines to fluidly connect the components of the kit.

The kit may comprise a collection channel fluidly connectable to one of the first outlet and the second outlet of the microfluidic separation channel. The kit may comprise a collection vessel fluidly connectable to the collection channel. The kit may comprise a collection channel fluidly connectable to the first outlet and configured to recycle target cell enriched fluid or target cell depleted fluid to the microfluidic separation channel. The kit may comprise an intraluminal line fluidly connectable to one of the microfluidic separation channel and the first or the second outlet. The kit may comprise more than one microfluidic separation channel fluidly connectable to the source of the biofluid in parallel or in series. The kit may comprise one or more sensors or control modules connectable to the microfluidic separation channel.

The kit may include instructions to collect a biofluid, pretreat the biofluid by introducing a predetermined volume of additive into the source of the biofluid, flow the pretreated biofluid through the microfluidic separation channel, and apply acoustic energy to the separation channel. In some embodiments, the kit provides instructions to introduce the additive to alter or regulate the density of the biofluid or concentration of the target cells or non-target cells. The kit may comprise instructions to introduce a predetermined volume of the additive to control a desired density of the pretreated biofluid, as previously discussed herein. For instance, the kit may comprise instructions to introduce the additive to regulate the density of the biofluid to a density of between about 1.04 g/mL and about 1.07 g/mL. The kit may further comprise instructions to control the power, voltage, or frequency of the acoustic transducer to alter or regulate the HCT %, concentration of target cells or concentration of non-target cells in the output suspension, as previously discussed herein. For instance, the kit may comprise instructions to regulate the output suspension HCT % to be less than about 10%. The kit may comprise instructions to perform any step or collection of steps from the method of separating target cells from non-target cells.

The function and advantages of the embodiments discussed above and other embodiments of the invention can be further understood from the description of the figures below, which further illustrate the benefits and/or advantages of the one or more systems and techniques of the invention but do not exemplify the full scope of the invention.

As shown in the exemplary concept schematic drawing of FIG. 1, a biofluid comprising target cells 18 and non-target cells 16 and 20 is flowed through microfluidic separation channel 28, through the inlet 10. Acoustic energy is applied to the separation channel 28 within the illustrated dotted line rectangle. Acoustic energy may be applied by attaching a piezoelectric transducer (not shown) to one wall of the separation channel. Target cells 18 accumulate within primary stream 32 and exit the separation channel 28 through first outlet 14. Target cell enriched fluid exits the first outlet 14. Non-target cells 16 and 20 accumulate within secondary stream 30 and exit the separation channel through second outlet 12. The non-target cells 18 and 20 are contained in a waste fluid. In some embodiments, the target cell enriched fluid within the primary stream 32 is collected.

Figure 2:
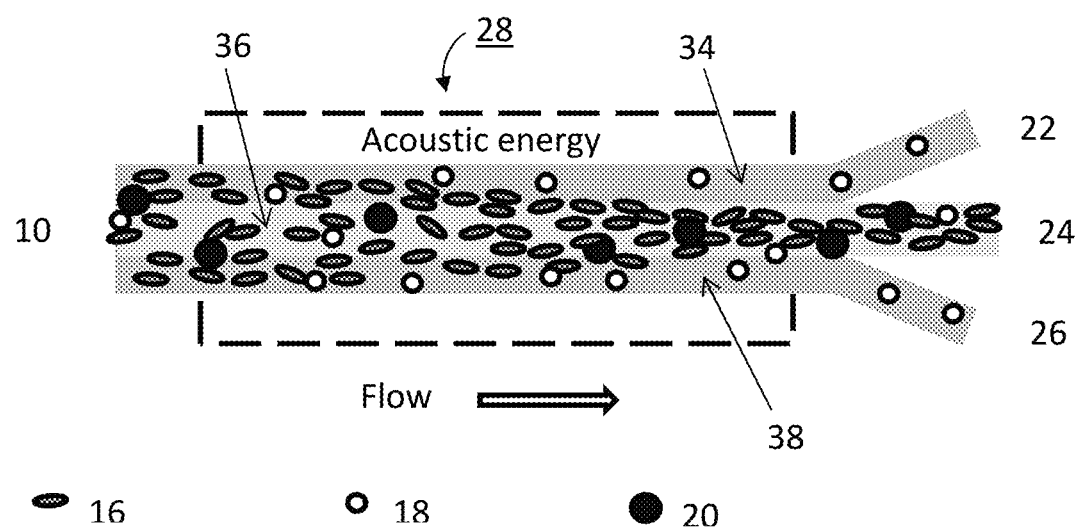
FIG. 2 is a schematic drawing of an alternate microfluidic separation channel, according to another embodiment.

Similarly, as shown in the exemplary concept schematic drawing of FIG. 2, the biofluid comprising target cells 18 and non-target cells 16 and 20 is flowed through the microfluidic separation channel 28 through inlet 10. In the embodiment exemplified in FIG. 2, target cells 18 essentially accumulate within two primary streams, 34 and 38, at the periphery of the separation channel 28, upon being subjected to the acoustic energy. Non-target cells 16 and 20 essentially accumulate within the central secondary stream 36. The primary streams 34 and 38 (target cell enriched fluid) exit the separation channel 28 through peripheral first outlets 22 and 26, while the secondary stream 36 (waste fluid) exits the separation channel 28 through second outlet 24. In this exemplary embodiment, non-target cells 16 and 20 are more susceptible to the acoustic energy, so they travel rapidly to the central region (secondary stream 36) of the separation channel 28, while the target cells 18 experience a weaker force from the acoustic energy and remain in the peripheral region of the separation channel 28 (primary streams 34 and 38).

Figure 3:
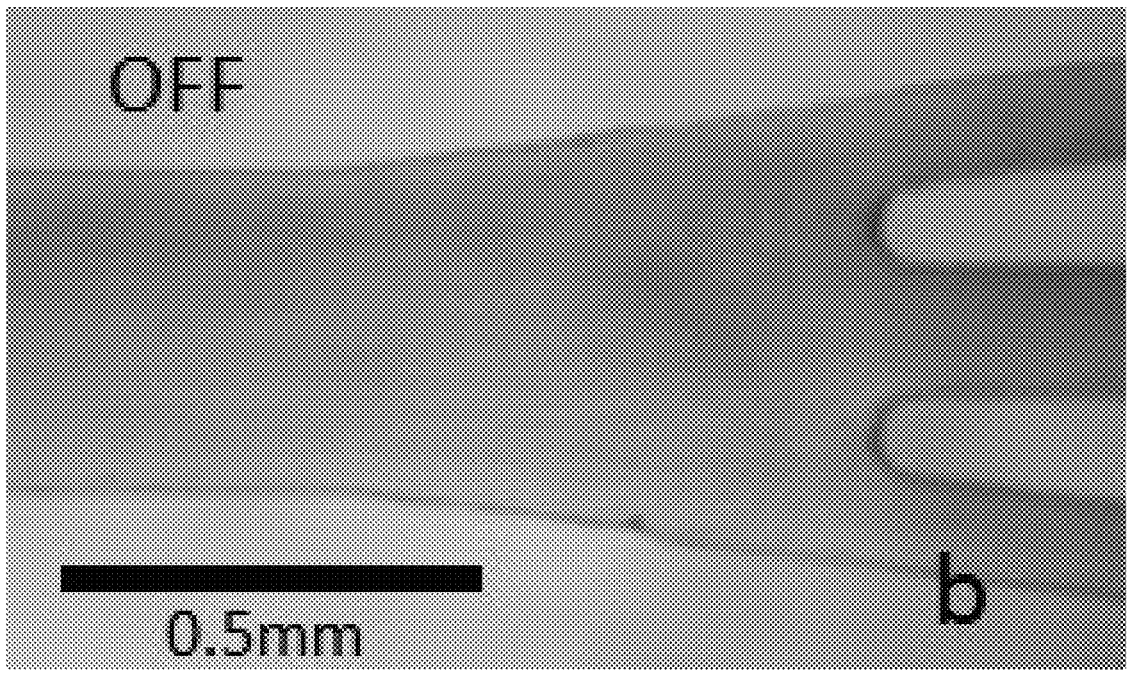
FIG. 3 is a micrograph of a microfluidic separation channel coupled to an acoustic transducer that is turned off.
Figure 4:
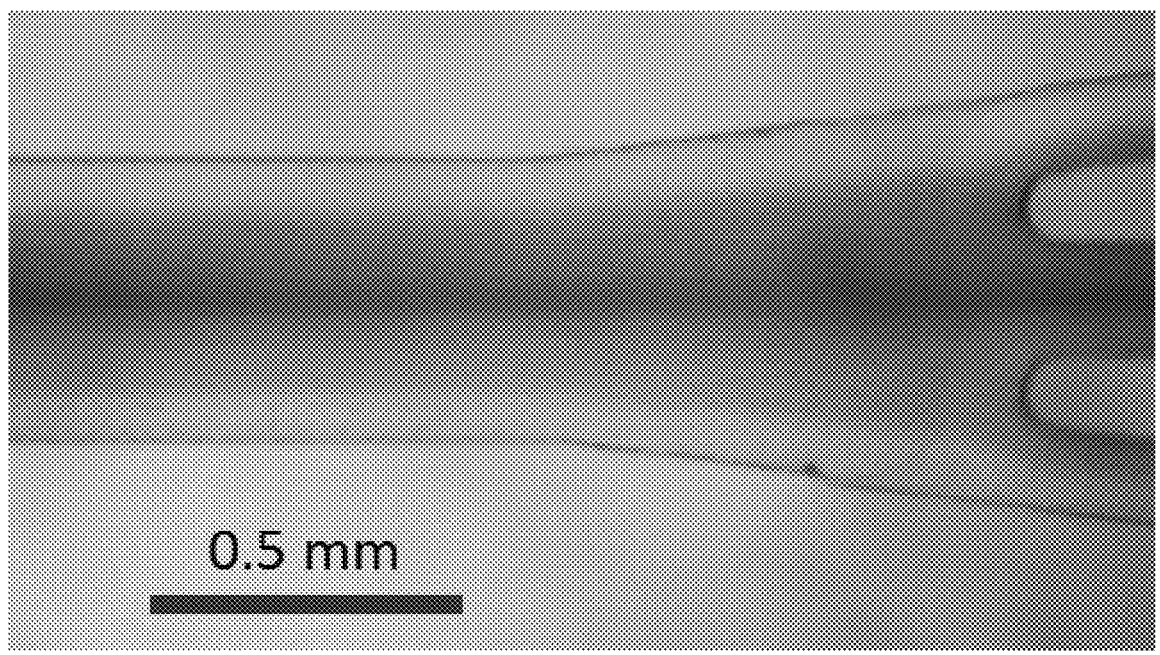

FIG. 3 and FIG. 4 are microscopic images of the downstream end of a microfluidic separation channel. In FIG. 3, the microfluidic separation channel is receiving no acoustic energy. As shown in the image, a homogeneous cell suspension is flowing through the channel with no separation. In FIG. 4, the microfluidic separation channel is receiving acoustic energy. Non-target cells, shown as the darker shade, can be seen traveling through the center stream, while target cells (not individually visible in the images) travel through the outer streams. The separation as seen in FIG. 4 is much greater than that seen in FIG. 3.

Figure 5:
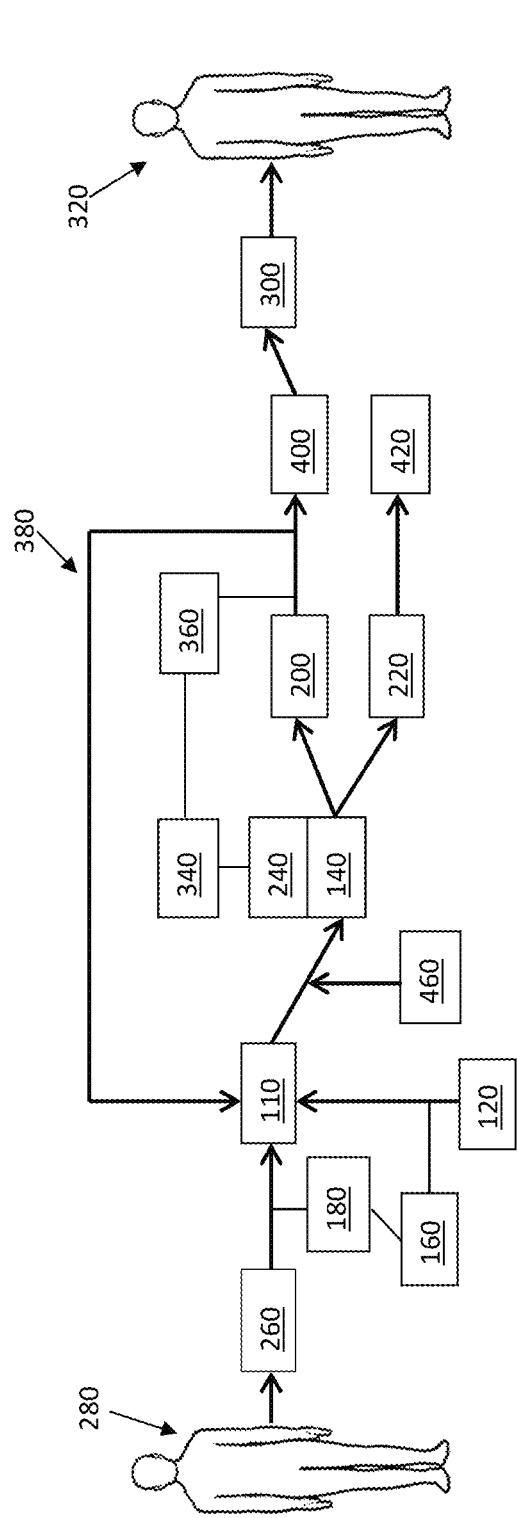
FIG. 5 is a schematic drawing of a system for microfluidic cell separation, according to one embodiment.

As shown in FIG. 5, according to certain embodiments, a system for microfluidic separation of target cells and non-target cells in a biofluid may comprise a source of a biofluid 110, a source of an additive 120, and a microfluidic separation channel 140 coupled to an acoustic transducer 240. The system may further comprise a sensor 180 configured to measure a parameter of an input biofluid and a sensor 360 configured to measure a parameter of a primary stream. The sensors may be electrically connected to control modules 340 and 160, such that control module 340 is configured to alter or regulate an input parameter of the acoustic transducer 240 and the control module 160 is configured to introduce a predetermined volume of the additive into the biofluid. While not shown, the system may include more than one source of an additive. Similarly, the system may include more than one sensor configured to measure the biofluid and/or more than one sensor configured to measure an output parameter. Additionally, while two control modules 340, 160 are shown in the exemplary system of FIG. 5, a single control module or more than two control modules may be electrically connected to the sensors.

The system may further comprise intraluminal line 260 fluidly connected to donor subject 280 and second intraluminal line 300 fluidly connected to recipient subject 320. Recipient subject 320 and donor subject 280 may be the same subject. The microfluidic separation channel 140 may separate pretreated biofluid into a primary stream and a secondary stream, such that the primary stream comprising target cells (target cell enriched fluid) is directed to primary stream collection channel 220 and the secondary stream comprising non-target cells (target cell depleted fluid) is directed to secondary stream collection channel 220. The primary stream may be recycled back to the source of the biofluid 110 through recycle line 380 or may be post-treated in post-treatment chamber 400. In some embodiments, the post-treatment chamber 400 is fluidly connected to the intraluminal line 300. The secondary stream may be collected in collection vessel 420. The system may further comprise a source of a second fluid 460 fluidly connected to the microfluidic separation channel 140.

Figure 6:
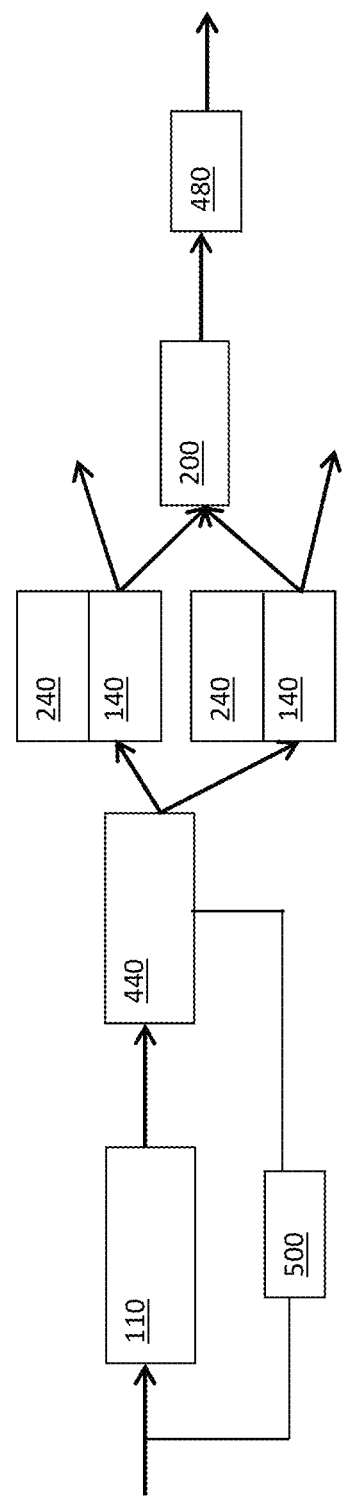
FIG. 6 is a schematic drawing of an alternate system for microfluidic cell separation, according to another embodiment.

Turning to FIG. 6, the system for microfluidic separation of target cells and non-target cells in a biofluid may further comprise two or more microfluidic separation channels 140. In the embodiment as shown, each microfluidic separation channel 140 is coupled to an acoustic transducer 240, however the system may comprise one acoustic transducer 240 coupled to more than one microfluidic separation channel 140. The two or more microfluidic separation channels 140 may be fluidly connected to a manifold 440, which may be fluidly or electrically connected to a sensor 500. The manifold 440 may be configured distribute the biofluid to the microfluidic separation channels 140 in response to a measurement received from the sensor 500 of an input biofluid load upstream of the biofluid source 110. In some embodiments, the system comprises a collection channel 200 downstream from the microfluidic separation channels 140 configured to collect the primary stream from the microfluidic separation channels 140. The system may further comprise a collection vessel 480 downstream from the collection channel 200.

Figure 14:
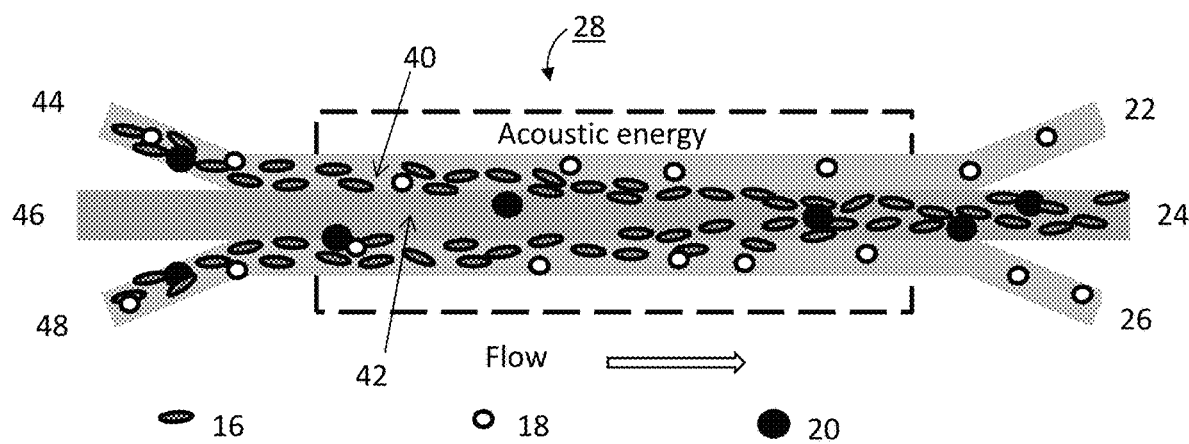
FIG. 14 is a schematic drawing of an alternate microfluidic separation channel, according to another embodiment.

As shown in exemplary concept schematic drawing of FIG. 14, a second fluid 42 may be flowed through the microfluidic separation channel 28 with pretreated biofluid 40, in essentially parallel flow. The second fluid 42 enters the microfluidic separation channel 28 through central inlet 46, while pretreated biofluid 40 enters the microfluidic separation channel 28 through peripheral inlets 44 and 48. The second fluid 42 does not comprise cells as it enters the separation channel 28. Non-target cells 16 and 20 are driven towards the center stream by the applied acoustic energy, and exit the separation channel through waste outlet 24. Target cells 18 are essentially buoyant within the microfluidic separation channel 28, and are not driven to the central stream. The estimated recovery in the exemplary embodiment of FIG. 14 is calculated to be about 70%. Comparatively, the estimated recovery in an embodiment without introducing a second fluid, such as the one exemplified in FIG. 2, is about 65%.

EXAMPLES

Example 1: Acoustic Separation for Purification of Lymphocytes

Separation of lymphocytes from human buffy coat product was performed with a microfluidic separation channel. The buffy coat was separated and collected from human whole blood. Buffy coat was flowed through a microfluidic separation channel at a residence time of about 1 second, and ultrasonic waves were applied to the channel to oscillate a portion of the channel having a cross section on the scale of the ultrasonic wavelength (~1 mm). The acoustic energy on the channel was applied to drive cells toward an axial center stream.

Lymphocytes experienced a weaker force than erythrocytes and other leukocytes, due to the difference between a lymphocyte's size and density as compared to the alternate cells. As the blood buffy coat was flowed through the channel and subjected to the acoustic energy, the lymphocyte population accumulated along primary streams at the outside of the channel, the lymphocyte enriched fluid was separated by a branching in the channel, for instance such as the one shown in FIG. 4. The lymphocyte enriched fluid was collected and analyzed.

Figure 9:
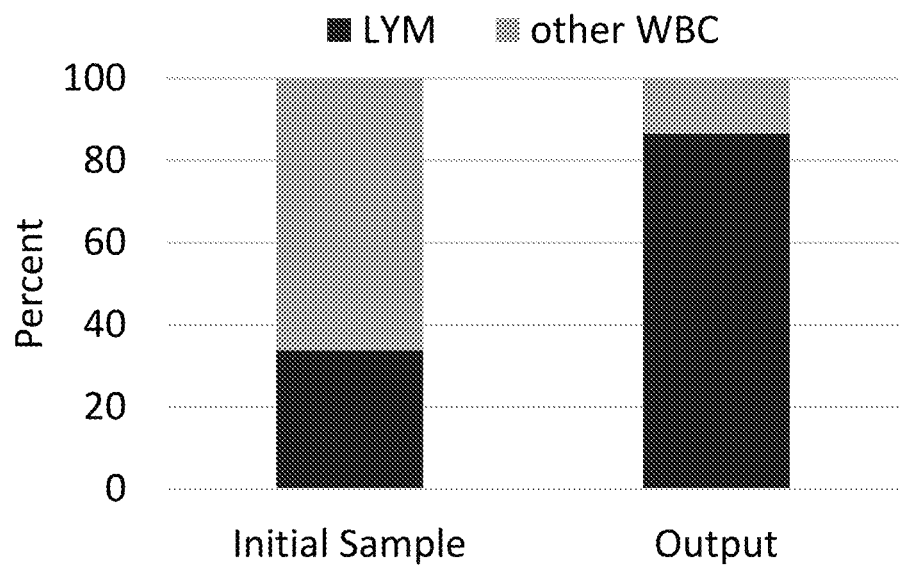
FIG. 9 is a graph of the relative population of lymphocytes among all white blood cells in a fraction collected after separation according to one embodiment of a method of separating cells in a biofluid.

Initial output cell counts were measured with a standard hematology analyzer. The results are shown in the graph of FIG. 9. In the lymphocyte enriched output suspension, lymphocyte population, as compared to other leukocytes, was enriched from 34% (initial population) to 87% (output population). Lymphocytes were enriched 2.5× by single pass through the microfluidic separation channel. Total lymphocyte recover was 21%. Erythrocyte concentration was reduced by 50%. Lymphocyte recovery and separation from erythrocytes can be increased with additives, by device tuning (e.g. tuning the input and/or output parameters of the acoustic transducer), and by performing repeat passes through the separation channel.

Generally, without wishing to be bound to a particular theory, it is believed that non-target cells are focused toward the center stream, while lymphocytes are weakly focused toward the center stream, allowing for retention in peripheral streams.

Accordingly, lymphocytes can be selectively separated from like cells (leukocytes) with the systems and methods described herein.

Example 2: Acoustic Separation with Density Gradient Medium

Blood buffy coat comprising lymphocytes and non-target cells was subjected to acoustic energy, generally as described above. Prior to flowing the buffy coat through a microfluidic separation channel, buffy coat samples were pretreated by diluting with a density gradient medium at diluent densities ranging between about 1.00 and 1.15 (g/mL). The results are measured in separation ratio, a quantitative measurement of the ratio of cells in the product (separation efficiency).

The separation Ratio for any subpopulation x, where "side" is the primary stream and "center" is the secondary stream.

$$SR_x = \frac{n_{x,side}}{n_{x,side} + n_{x,center}}$$

The fraction of the stream out the side channel (primary stream), also referred to as the flow split:

$$FR_{side} = \frac{V_{side}}{V_{center}}$$

Figure 10:
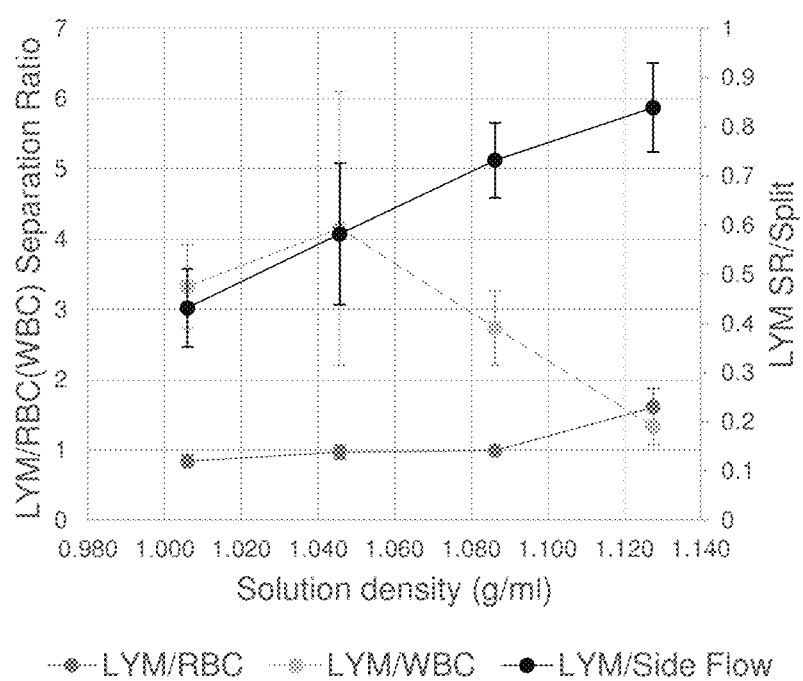
FIG. 10 is a graph of the separation ratio of lymphocytes to erythrocytes, leukocytes, or a side stream in a fraction collected after separation according to one embodiment of a method of separation cells in a biofluid.

The separation ratio results biofluid diluted with density gradient medium are summarized in the graph shown in FIG. 10. As shown, the density gradient medium provides efficient separation of lymphocytes from other leukocytes, but does not affect the separation of lymphocytes from erythrocytes, which remains constant around 1.0 for increasing solution density. A maximum separation of lymphocytes from other leukocytes is effectuated near the density of the lymphocytes (approximately 1.06 g/mL). Without wishing to be bound to a particular theory, it is believed the density gradient medium does not efficiently affect separation of cells from erythrocytes in this range because the density of the erythrocytes remains significantly higher than that of the suspending fluid.

Accordingly, lymphocyte separation from leukocytes in a biofluid can be performed with superior results by pretreating the biofluid with an additive, such as a density gradient medium. Without wishing to be bound to a particular theory, it is believed cell separation by pretreatment with additives capable of altering density of the biofluid, density of the target cells, density of the non-target cells, size of the target cells, size of the non-target cells, compressibility of the biofluid, compressibility of the target cells, compressibility of the non-target cells, aggregation potential of the target cells, and aggregation potential of the non-target cells will provide superior results over no pretreatment because the rate at which the cells migrate generally depends on cell size, density, and compressibility relative to the density and compressibility of the suspending biofluid.

Example 3: Acoustic Separation with Cell Aggregator

Blood buffy coat comprising lymphocytes and non-target cells was subjected to acoustic energy, generally as described above. Prior to flowing the buffy coat through a microfluidic separation channel, buffy coat samples were pretreated by introducing a cell aggregator. Specifically, Ficoll™ PM 300 cell media (GE Healthcare, Chicago, Ill.), a long-chain polysaccharide was introduced into the biofluid. The samples pretreated with a cell aggregator were compared to samples pretreated with a density gradient medium, as described above (pretreated with Histopaque® media distributed by Sigma-Aldrich, St. Louis, Mo.).

Figure 13:
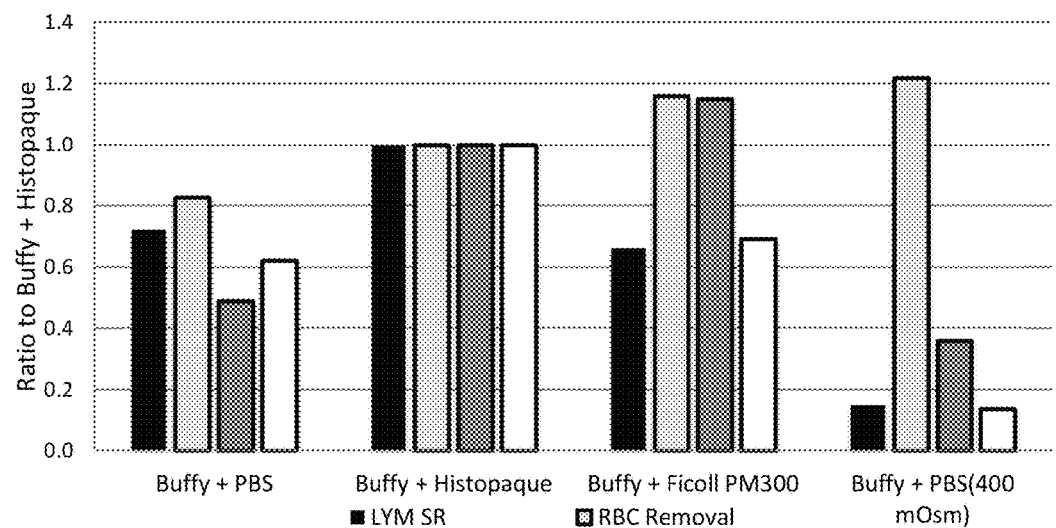
FIG. 13 is a comparison graph of lymphocyte separation ratio and erythrocyte removal from samples pretreated with a cell aggregator as compared to samples pretreated with a density gradient medium, according to one embodiment of a method of separating cells in a biofluid.

The results are summarized in the graph of FIG. 13. The samples pretreated with a cell aggregator exhibited better erythrocyte removal than the samples pretreated with a density gradient medium. However, the cell aggregator samples exhibited lower lymphocyte recovery than the density gradient medium samples. Nonetheless, both the cell aggregator samples and the density gradient medium samples exhibited improved erythrocyte removal and lymphocyte recovery than the control sample pretreated with PBS alone.

Accordingly, pretreating the biofluid with a cell aggregator provides superior non-target cell removal, but inferior target cell recovery, than pretreating the biofluid with a density gradient medium. Furthermore, lymphocyte separation from leukocytes in a biofluid can be performed with superior results by pretreating the biofluid with a density gradient medium or a cell aggregator, as compared to pretreating the biofluid with PBS alone.

Example 4: Acoustic Separation with Density Gradient Medium and Cell Aggregator Blood buffy coat comprising lymphocytes and non-target cells was subjected to acoustic energy, generally as described above. Prior to flowing the buffy coat through a microfluidic separation channel, buffy coat samples were pretreated by diluting with an additive comprising a density gradient medium and cell aggregator to provide a solution density ranging between about 1.00 and 1.10 (g/mL). Specifically, the samples were pretreated with Histopaque® media (Sigma-Aldrich, St. Louis, Mo.).

Figure 11:
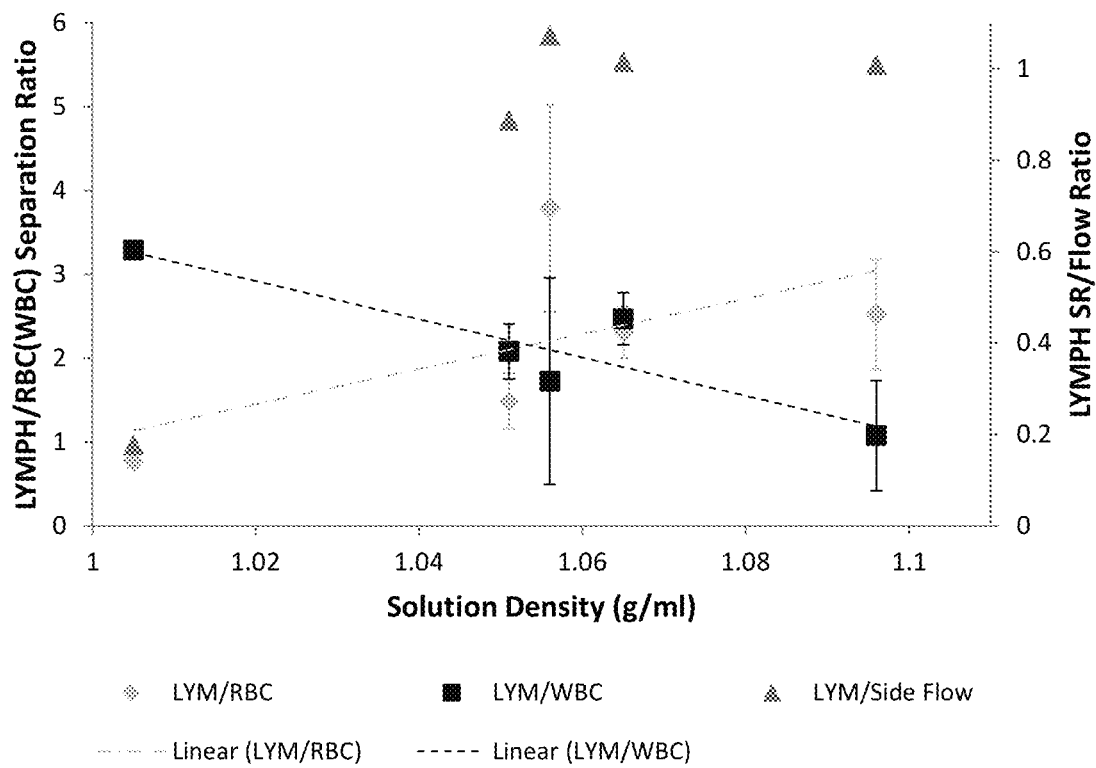
FIG. 11 is a graph of the separation ratio of lymphocytes to erythrocytes, leukocytes, or a side stream in a fraction collected after separation according to an alternate embodiment of a method of separation cells in a biofluid.

The results are summarized in the graph of FIG. 11. The graph shows a much better enrichment of lymphocytes from erythrocytes, as compared to the density gradient medium alone (FIG. 10). The lymphocyte/erythrocyte trendline shows that the additive comprising a density gradient medium and a cell aggregator displays a generally increasing separation of lymphocytes from erythrocytes with increasing solution density. In contrast, the lymphocyte/leukocyte trendline displays a generally decreasing separation of lymphocytes from leukocytes with increasing solution density. The optimal solution density is the point at which the trendlines cross, or near 1.06 g/mL, which is the approximate density of the lymphocytes. Accordingly, lymphocytes can be separated from erythrocytes and leukocytes most efficiently with an additive configured to alter the solution density to about 1.06 g/mL.

Furthermore, lymphocyte separation from erythrocytes and leukocytes in a biofluid is more efficient when the biofluid is pretreated with both a density gradient medium and a cell aggregator. The data show there is a synergistic result for the combination of mediums when compared to cell separation with each medium alone.

Example 5: Separation of Lymphocytes with Addition of a Density Gradient Medium Blood plasma comprising lymphocytes and non-target cells was subjected to acoustic energy, generally as described above. Prior to flowing the blood plasma through a microfluidic separation channel, plasma samples were pretreated by diluting with an additive comprising a density gradient medium to provide experimental samples having solution densities ranging between about 1.04 and 1.06 (g/mL) and a control sample having a solution density averaging about 1.08 g/mL. Specifically, the samples were pretreated with Histopaque® media (Sigma-Aldrich, St. Louis, Mo.) to regulate their density.

Surprisingly, the samples having a specific density between about 1.04 and 1.06 g/mL exhibited better purification of lymphocytes. These results were surprising because conventional density medium separation by centrifugation teaches a target density closer to 1.08 g/mL, which is the average density of mononuclear cells. Thus, by regulating the biofluid density to be slightly different than the density of the average target cells (here about 0.02 g/mL to 0.04 g/mL less than the average density of lymphocytes) better purification may be achieved.

Example 6: Separation of T Cells from B Cells by Addition of a B Cell Activator A suspension of white blood cells comprising T cells and B cells was subjected to acoustic energy, generally as described above. Prior to flowing the suspension through a microfluidic separation channel, samples were pretreated by diluting with an additive comprising a B cell activator, CpG ODN. The samples were incubated for one to three days before starting the acoustic separation.

While not wishing to be bound by any particular theory, it is believed the CpG ODN activated the B cells, thereby enlarging them. The activated B cells were focused more strongly by the acoustic field to the center channel and depleted, while desired T cells remained in the channel side streams. Thus, B cells may be separated from T cells by addition of a B cell activator, here CpG ODN.

Example 7A: Separation of Platelets from Lymphocytes by Addition of a Platelet Activator—Blood Sample A blood sample comprising lymphocytes and platelets was subjected to acoustic energy, generally as described above. Prior to flowing the blood sample through a microfluidic separation channel, the blood sample was pretreated by diluting with an additive comprising a platelet activator, adenosine diphosphate. Adenosine diphosphate was added at a concentration of 2-50 µM. The samples were incubated for 10-20 minutes before starting the acoustic separation.

While not wishing to be bound by any particular theory, it is believed the adenosine diphosphate activated the platelets, thereby inducing them to release CAMs and aggregate into clusters and/or adhere to other cells. The aggregated platelets responded more strongly to the acoustic field than individual platelets. Thus, platelets may be separated from lymphocytes by addition of a platelet activator, here adenosine diphosphate. It is believed platelets can be separated from other particles in the blood sample by a similar method. For instance, it is believed platelets can be separated from bacteria by a similar method.

Example 7B: Separation of Platelets from Lymphocytes by Addition of a Platelet Activator—Blood Buffy Coat Sample Conventionally, it is difficult to purify lymphocytes from a sample containing platelets with acoustic energy. While lymphocyte recovery is high, the collected biofluid typically contains a high concentration of platelets as well. Platelet activation may aggregate platelets into clusters from which the lymphocytes are separable with acoustic energy.

Blood buffy coat samples from 3 donors (comprising lymphocytes and platelets) were subjected to acoustic energy, generally as described above. Prior to flowing the blood buffy coat samples through a microfluidic separation channel, the blood buffy coat samples were pretreated. Experimental samples were treated with 8 µM adenosine diphosphate (ADP) in buffer and control samples were treated with buffer only to a final dilution of approximately 1:3 buffy coat:buffer (about $10^9$ cells/ml). The samples were incubated for 5 min before separation.

The samples were flowed at 0.1 ml/min through a single polystyrene microchannel mounted on an oscillator using the methods described herein. The acoustic force displaced larger and more dense cells and platelet cell aggregates toward a center outlet (waste) while side outlets collected the lymphocyte-enriched product, generally as shown in FIG. 15. The products were compared to the input solution using both a hematology analyzer (Sysmex Corporation, Kobe, Hyogo Prefecture, Japan) to count cells and ELISA of the platelet-specific glycoprotein IIb/IIIa.

Introduction of ADP strongly reduced platelet contamination in the collected lymphocytes when compared to controls. Acoustic treatment in controls pushed large cells to the center (waste) outlet and enriched lymphocytes, but also displaced platelets to the periphery and into the product.

Figure 16:
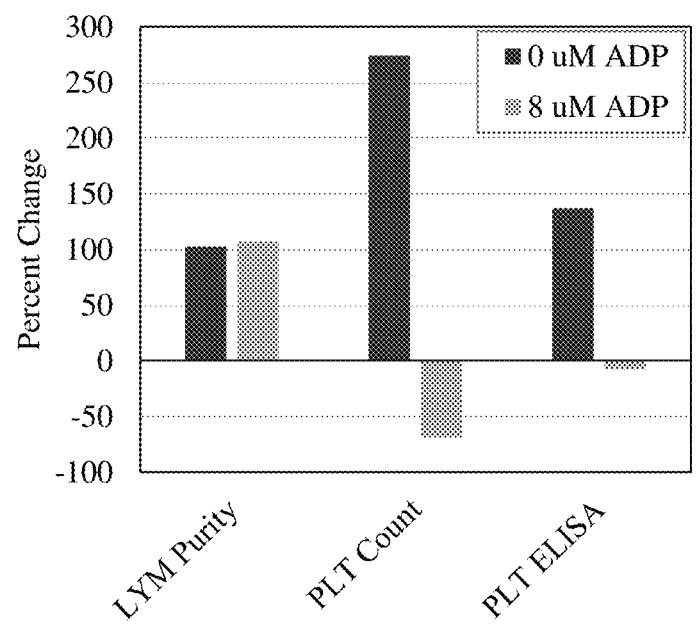
FIG. 16 is a graph showing percent change of lymphocyte and platelet removal from samples pretreated with a platelet activator as compared to samples pretreated with control buffer, according to one embodiment of a method of separating cells in a biofluid.

In contrast, as shown in the data presented in the graph of FIG. 16, ADP at 8 µM reduced platelet count in the product nearly ten-fold, from 274% increase to 69% decrease compared to the starting material. The glycoprotein IIb/IIIa assay also showed significantly reduced platelet content. Hematocrit was depleted to 4.5% from 10%. Meanwhile, collection of lymphocytes remained robust with or without ADP added, from an input purity of 41% to an output 84% (% WBC), a 104% increase.

Notably, increasing ADP to 32 µM did not further improve platelet depletion. The methods may comprise pretreating the biofluid with ADP in a concentration of between about 5 µM and about 30 µM, for example, between about 8 µM and about 20 µM. For instance, 10 µM ADP produces platelet aggregates having a diameter of about 10 µm.

Addition of ADP aids platelet depletion without interfering with acoustic lymphocyte collection. It is estimated that induced cell aggregation by various methods may extend the classes of cells that can be isolated by acoustic separation. For example, biochemically induced aggregation and/or activation may improve acoustic separation of cells that have previously been difficult to discriminate by their size alone.

Example 8: Separation of Activated T Cells from Resting T Cells by Addition of a T Cell Activator to a Portion of the Sample A suspension comprising activated T cells and resting (non-activated) T cells was subjected to acoustic energy, generally as described above. Prior to flowing the suspension through a microfluidic separation channel, a portion of a T cell sample was pretreated by diluting with an additive comprising a T cell activator, bead coated with humanized CD3 and CD28 agonist antibodies, here TransAct™ beads (Miltenyi Biotec). The pretreated portion was then recombined with the remainder of the T cell sample (untreated) to create the suspension comprising activated T cells and resting T cells.

While not wishing to be bound by any particular theory, it is believed the T cell TransAct™ beads activated the pretreated T cells, thereby enlarging them. After the acoustic separation, enrichment of activated T cells was observed through the center channel, relative to the outer channels. The activated T cells were believed to have responded more strongly to the acoustic field than resting T cells because of their larger size. Thus, activated T cells may be separated from resting T cells by acoustic separation. It is believed other cell types may be separated into activated cells and resting cells by treating a portion of a sample with the appropriate activator.

Conclusion—Comparative Results

In similar lymphocyte separation experiments, biofluid diluted with a long-chain polysaccharide (cell aggregator) and PBS experienced better erythrocyte removal, but lower lymphocyte recovery than biofluid samples diluted in a density gradient medium and a cell aggregator. Biofluid diluted with high salt PBS (400 mOsm PBS) experienced better erythrocyte removal, but lower lymphocyte recovery when compared to biofluid diluted in the density gradient medium and cell aggregator. Finally, biofluid diluted in isotonic PBS experienced decreased performance across all metrics, when compared to biofluid diluted in the density gradient medium and cell aggregator, and generally as compared to the other experimental samples.

Accordingly, pretreating biofluid with an additive may result in increased separation between target cells and non-target cells, as compared to acoustic separation of biofluid alone.

Figure 12:
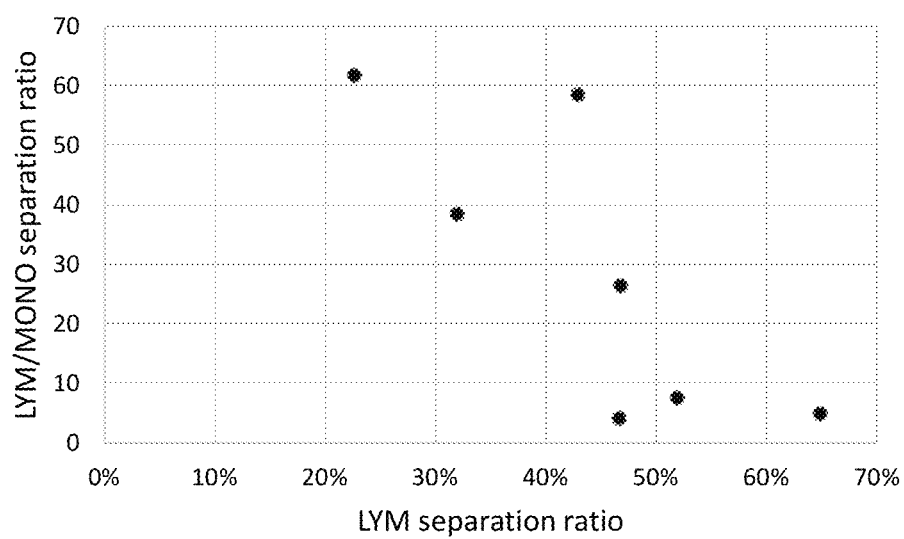
FIG. 12 is a graph comparing lymphocyte to monocyte separation ratio in the fraction collected after separation, according to one embodiment of a method of separating cells in a biofluid.

Example 9: Comparison Between Target Cells—Lymphocyte and Monocyte Separation Ratio Biofluid comprising lymphocytes and monocytes was flowed through a microfluidic separation channel and subjected to acoustic energy. The lymphocyte separation ratio was calculated as previously discussed. The monocyte separation ratio was compared to the lymphocyte separation ratio. The results are shown in the graph of FIG. 12. The data suggest that there is a differential separation between monocytes and lymphocytes. The results are significant because other separation processes, for example centrifugation, do not separate lymphocytes from monocytes. Accordingly, systems and methods disclosed herein allow for differential separation between cell types, including between different classes of leukocytes.

Example 10: Comparison Between Biofluids—Lymphocyte Purity and Recovery from Leukapheresis Product, Buffy Coat, and Whole Blood Acoustic separation of lymphocytes from biofluid samples was performed, generally as described above. The biofluid samples included leukapheresis product, blood buffy coat, and whole blood. Generally, leukapheresis product comprises the highest ratio of leukocytes to other cells, blood buffy coat comprises a mid-range ratio of leukocytes to other cells, and whole blood comprises the lowest ratio of leukocytes to other cells. Accordingly, as expected, lymphocyte recovery (percentage of lymphocyte in product to lymphocyte in biofluid sample), and lymphocyte purity (as a fraction of lymphocyte to total leukocyte concentration) is greatest when the biofluid is selected to be leukapheresis product, of the three example biofluids.

Figure 7:
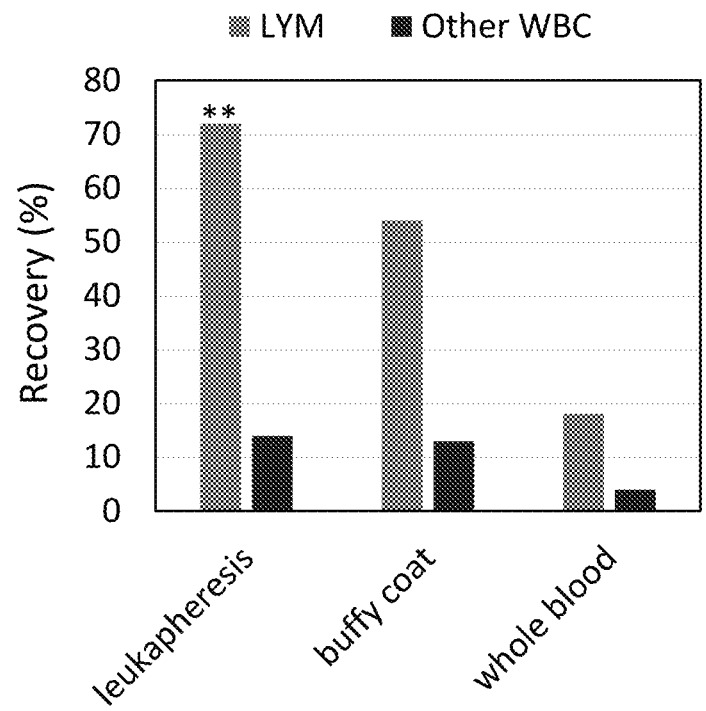
FIG. 7 is a graph of the percentage of recovery for lymphocytes and other white blood cells from leukapheresis fluid, buffy coat, and whole blood after separation according to one embodiment of a method of separating lymphocytes and white blood cells from other cells in a biofluid.
Figure 8:
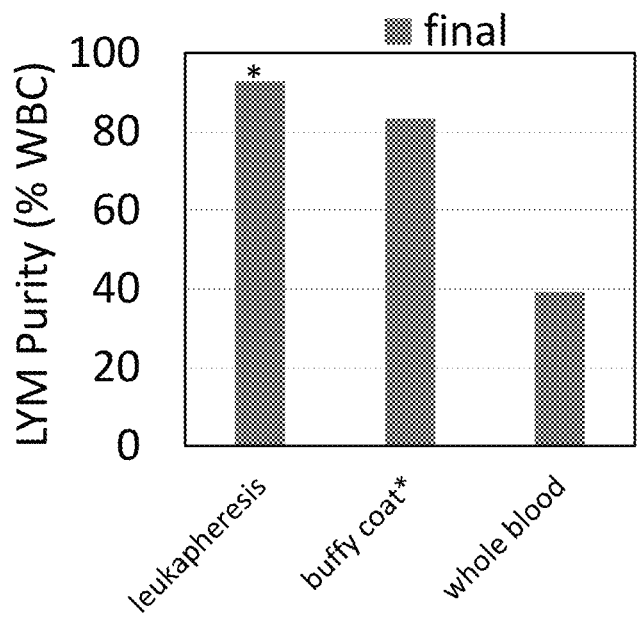
FIG. 8 is a graph of lymphocyte purity as a percentage of all white blood cells from leukapheresis fluid, buffy coat, and whole blood after separation according to one embodiment of a method for separating lymphocytes from other cells in a biofluid.

As shown in the results presented in the graphs of FIGS. 7 and 8, lymphocyte recovery from leukapheresis product, buffy coat, and whole blood is 71%, 54%, and 18%, respectively. Lymphocyte purity in these samples was high, at 93%, 83%, and 39%, respectively. Furthermore, the separation provided erythrocyte reduction (percentage of erythrocyte reduced from the biofluid sample) of about 94%, depending on the recovery goal. Accordingly, systems and methods for cell separation, as disclosed herein, may effectively recover and purify biofluid samples of various purities with a first pass acoustic separation process.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for microfluidic cell separation. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure, and are intended to be within the spirit and scope of the disclosure. In other instances, an existing facility may be modified to utilize or incorporate any one or more aspects of the methods and systems described herein. Thus, in some instances, the systems may involve microfluidic cell separation. Accordingly the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the following claims.

What is claimed is:

1. A method of separating target cells from non-target cells in a biofluid, comprising:
    selecting the target cells to be a desired cell type;
    pretreating the biofluid comprising mixed cells by introducing an additive to alter at least one of size of the target cells, size of the non-target cells, compressibility of the biofluid, compressibility of the target cells, compressibility of the non-target cells, aggregation potential of the target cells, and aggregation potential of the non-target cells, the additive comprising a cell activator;
    flowing the pretreated biofluid into an inlet of a microfluidic separation channel; and applying acoustic energy to the pretreated biofluid within the microfluidic separation channel, such that the target cells accumulate within at least one primary stream along the separation channel and the non-target cells accumulate within at least one secondary stream along the separation channel.

2. The method of claim 1, comprising selecting the cell activator to comprise a B cell activator.

3. The method of claim 2, wherein the B cell activator comprises CpG oligodeoxynucleotides.

4. The method of claim 1, comprising selecting the cell activator to comprise a T cell activator.

5. The method of claim 4, wherein the T cell activator comprises at least one of a soluble CD3 antibody, a bead coated with humanized CD3 and CD28 agonist antibodies, and Interleukin 2.

6. The method of claim 1, wherein the additive comprises at least one of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

7. The method of claim 6, further comprising selecting the additive to be a platelet activator or a cell adhesion molecule.

8. The method of claim 7, further comprising selecting the additive to be adenosine diphosphate.

9. A system for microfluidic cell separation configured to separate target cells from non-target cells in a biofluid, comprising:
at least one microfluidic separation channel comprising an inlet, a first outlet, and a second outlet;
a source of the biofluid comprising the target cells and the non-target cells in fluid communication with the inlet of the at least one microfluidic separation channel;
a source of a predetermined volume of an additive comprising a cell activator in fluid communication with the source of the biofluid, the additive being effective to alter at least one of size of the target cells, size of the non-target cells, compressibility of the biofluid, compressibility of the target cells, compressibility of the non-target cells, aggregation potential of the target cells, and aggregation potential of the non-target cells; and
at least one acoustic transducer coupled to a wall of the at least one microfluidic separation channel positioned and configured to apply a standing acoustic wave transverse to the microfluidic separation channel at selected parameters including wavelength, frequency, amplitude, and power level effective to accumulate the target cells within at least one primary stream along the microfluidic separation channel directed to the first outlet and accumulate the non-target cells within at least one secondary stream along the microfluidic separation channel directed to the second outlet.

10. The system of claim 9, wherein the cell activator comprises a B cell activator.

11. The system of claim 10, wherein the B cell activator comprises CpG oligodeoxynucleotides.

12. The system of claim 9, wherein the cell activator comprises a T cell activator.

13. The system of claim 12, wherein the T cell activator comprises at least one of a soluble CD3 antibody, a bead coated with humanized CD3 and CD28 agonist antibodies, and Interleukin 2.

14. The system of claim 9, wherein the additive comprises at least one of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

15. The system of claim 14, wherein the additive comprises a platelet activator or a cell adhesion molecule.

16. The system of claim 15, wherein the additive comprises adenosine diphosphate.

17. The system of claim 9, further comprising at least one input sensor configured to measure a concentration of target cells or non-target cells in the biofluid.

18. The system of claim 17, further comprising at least one output sensor configured to measure at least one parameter of an output suspension, the at least one parameter comprising at least one of hematocrit (HCT %) of the output suspension, concentration of target cells in the output suspension, and concentration of non-target cells in the output suspension.

19. The system of claim 18, further comprising a control module in electrical communication with the at least one input sensor, the at least one output sensor, and the source of the additive, configured to introduce the predetermined volume of the additive into the biofluid in response to a measurement of at least one of the concentration of the target cells or the non-target cells in the biofluid and the parameter of the output suspension being outside tolerance of a target value.

20. A method of separating target cells from non-target cells in a biofluid, comprising:
selecting the target cells to be leukocytes selected from the group consisting of mononuclear cells, lymphocytes, monocytes, granulocytes, agranulocytes, macrophages, T cells, B cells, NK cells, subclasses thereof, and combinations thereof;
pretreating the biofluid comprising mixed cells by introducing a predetermined volume of an additive effective to alter at least one of size of the target cells, size of the non-target cells, compressibility of the biofluid, compressibility of the target cells, compressibility of the non-target cells, aggregation potential of the target cells, and aggregation potential of the non-target cells, the additive comprising a cell activator;
flowing the pretreated biofluid into an inlet of a microfluidic separation channel; and
applying acoustic energy to the pretreated biofluid comprising the mixed cells within the microfluidic separation channel, such that the target cells accumulate within at least one primary stream along the separation channel and the non-target cells accumulate within at least one secondary stream along the separation channel.

21. The method of claim 20, further comprising selecting the target cells to be a class of lymphocytes.

* * * * *